US012589072B2

(12) United States Patent
Abu Ammar et al.

(10) Patent No.: US 12,589,072 B2
(45) Date of Patent: Mar. 31, 2026

(54) BIOADHESIVE FILM AND METHODS OF USE THEREOF

(71) Applicants: HADASIT MEDICAL RESEARCH SERVICES AND DEVELOPMENT LTD., Jerusalem (IL); AZRIELI COLLEGE OF ENGINEERING JERUSALEM, Jerusalem (IL)

(72) Inventors: Aiman Abu Ammar, Baqa Algharbiya (IL); Haytam Kasem, Iksal (IL)

(73) Assignees: HADASIT MEDICAL RESEARCH SERVICES AND DEVELOPMENT LTD., Jerusalem (IL); AZRIELI COLLEGE OF ENGINEERING JERUSALEM, Jerusalem (IL)

( * ) Notice: Subject to any disclaimer, the term of this patent is extended or adjusted under 35 U.S.C. 154(b) by 419 days.

(21) Appl. No.: 18/036,326

(22) PCT Filed: Nov. 11, 2021

(86) PCT No.: PCT/IL2021/051345
§ 371 (c)(1),
(2) Date: May 10, 2023

(87) PCT Pub. No.: WO2022/101911
PCT Pub. Date: May 19, 2022

(65) Prior Publication Data
US 2024/0041759 A1 Feb. 8, 2024

Related U.S. Application Data

(60) Provisional application No. 63/112,209, filed on Nov. 11, 2020.

(51) Int. Cl.
*A61K 9/00* (2006.01)
*A61K 45/06* (2006.01)

(52) U.S. Cl.
CPC ............ *A61K 9/006* (2013.01); *A61K 9/0004* (2013.01); *A61K 45/06* (2013.01)

(58) Field of Classification Search
None
See application file for complete search history.

(56) References Cited

U.S. PATENT DOCUMENTS

2017/0196819 A1    7/2017 Liu

FOREIGN PATENT DOCUMENTS

| AU | 2014200648 A1 | 2/2014 |
| CN | 111303631 A | 6/2020 |
| WO | 2014025792 A1 | 2/2014 |

OTHER PUBLICATIONS

Roque Let al.: "Mucoadhesive assessment of different antifungal nanoformulations"; Bioinspir Biomim, vol. 13, No. 5, p. 055001 (manuscript version pp. 1-32), DOI: 10.1088/I 748-3190/aad488, Aug. 5, 2018 (Aug. 5, 2018) (Year: 2018).*
Mahdavi, Alborz, et al. "A biodegradable and biocompatible gecko-inspired tissue adhesive." Proceedings of the National Academy of Sciences 105.7 (2008): 2307-2312. https://doi.org/10.1073/pnas.0712117105.
Gorb, Stanislav N., and Michael Varenberg. "Mushroom-shaped geometry of contact elements in biological adhesive systems." Journal of Adhesion Science and Technology 21.12-13 (2007): 1175-1183. https://doi.org/10.1163/156856107782328317.
Roque et al (2018) Mucoadhesive assessment of different antifungal nanoformulations, Bioinspir Biomim 13 (5):055001. doi: 10.1088/1748-3190/aad488. PMID: 30024385.
Kim et al (2019) Design and Evaluation of Poly(Lactide-co-Glycolide)-Based In Situ Film-Forming System for Topical Delivery of Trolamine Salicylate, Pharmaceutics 11(8):409. 10.3390/pharmaceutics11080409.
Modaresifar et al (2015) Nano-Biomimetic Tissue Adhesives Development: From Research to Clinical Application, Polymer Reviews 56(2):329-361, DOI: 10.1080/15583724.2015.1114493.
Wang et al (2019) Gecko toe pads inspired in situ switchable superhydrophobic shape memory adhesive film, Nanoscale 11(18):8984-8993, DOI https://doi.org/10.1039/C9NR00154A.
Abdel-Haq et al (2021) Biomimetic clotrimazole-loaded PLGA films with enhanced adhesiveness for controlled drug release, Int J Pharm, vol. 601, article 120578, pp. 109, doi: 10.1016/j.ijpharm.2021.120578. Epub Apr. 9, 2021. PMID: 33839222.
Abu Ammar et al (2021) Developing Novel Poly(Lactic-Co-Glycolic Acid) (PLGA) Films with Enhanced Adhesion Capacity for Biomimetic Mushroom-shaped Microstructures, Biotribology, vol. 27, p. 100184, DOI:10.1016/j.biotri.2021.100184.
Del Campo et al (2007) Patterned Surfaces with pillars with controlled 3 tip geometry mimicking bioattachment devices, Adv Mater, 19(15):1973-1977, DOI:10.1002/adma.200602476.
PCT International Search Report for International Application No. PCT/IL2021/051345, mailed Jan. 17, 2022, 4pp.
PCT Written Opinion for International Application No. PCT/IL2021/051345, mailed Jan. 19, 2022, 9pp.
PCT International Preliminary Report on Patentability for International Application No. PCT/IL2021/051345, issued May 16, 2023, 10pp.

* cited by examiner

*Primary Examiner* — Robert A Wax
*Assistant Examiner* — Andre Mach
(74) *Attorney, Agent, or Firm* — The Roy Gross Law Firm, LLC; Roy D. Gross

(57) ABSTRACT

A film and a method for use thereof such as for the administration of a biologically active agent or for therapy are provided. Specifically, a film, composed of a biodegradable material having a mucoadhesive surface comprising a plurality of mushroom-type structures is provided.

20 Claims, 22 Drawing Sheets

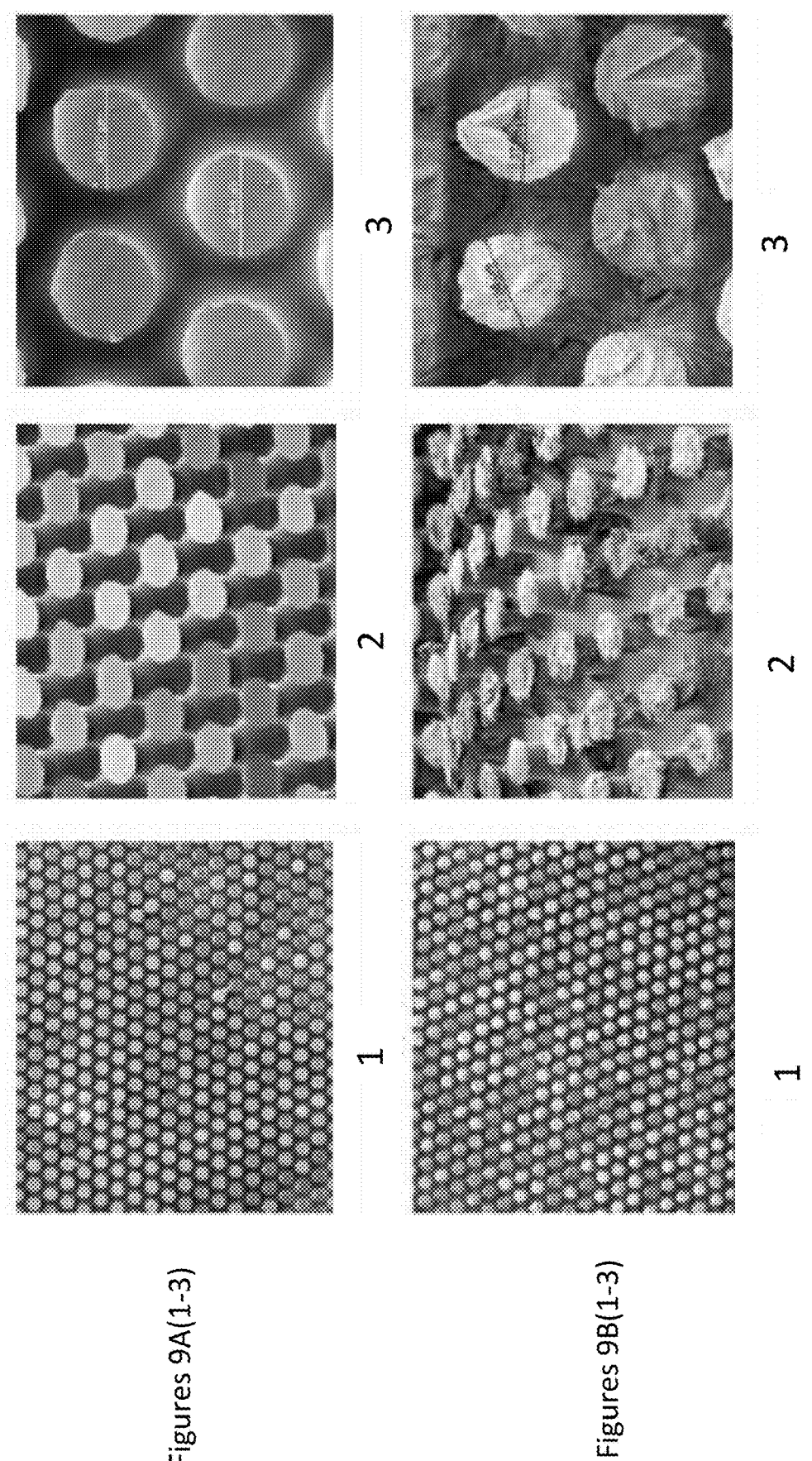
Figures 9A(1-3)
Figures 9B(1-3)

BIOADHESIVE FILM AND METHODS OF USE THEREOF

CROSS REFERENCE TO RELATED APPLICATIONS

This application is a National Phase of PCT Patent Application No. PCT/IL2021/051345 having International filing date of Nov. 11, 2021, which claims the benefit of priority of U.S. Provisional Patent Application No. 63/112, 209, filed Nov. 11, 2020, the contents of which are all incorporated herein by reference in their entirety.

FIELD OF THE INVENTION

The invention relates generally to the field of biodegradable adhesive materials and methods for use thereof such as in therapy or for delivery of an active agent.

BACKGROUND

Nature is a vast source to address different needs in many fields such as engineering, technology, and pharmaceutics. Mimicking biological systems by copying their physical and morphological features is used in product and process design.

Among the different traits of natural adaptation, the unique ability of locomotion and adherence of some animals and insects has aroused a strong interest for the development of rapid and reversible bio-inspired attachment technologies in response to increasing need during the last decades. Today's solutions have essentially been inspired by animals and insects like geckos, tree frogs, spiders, flies, and beetles. During their natural evolution they have developed fantastic biological attachment systems based on thin film elements of different forms. These allow them to adhere, run, and jump on walls and ceilings of even uneven surfaces. Furthermore, a development of bio-inspired smart surfaces with the function of controllable encapsulating and releasing of drugs can be used as a platform for sustained and localized release, leading to improved therapeutic outcome.

Several experimental studies reported in the literature, confirm that the physical functioning principle employed in the biological attachment systems of animals and insects can be exploited to design artificial surfaces with enhanced adhesion and friction capacity. Potential applications of such surfaces include climbing robotic systems, handling systems for wafers in nanofabrication facilities, mobile sensor platforms, and in liquid crystal display fabrication facilities. While efforts are being made to utilize bio-inspired patterned surfaces with enhanced adhesive properties for biomedical applications, they appear to be only in the early stages of development compared to other conventional uses.

Poly(lactic acid) (PLA), poly(glycolic acid) (PGA) and their copolymer PLGA) are aliphatic poly(esters). They are the best-known and characterized biodegradable synthetic materials with many years of clinical use. PLGA is an FDA-approved copolymer with a wide range of physico-chemical and mechanical properties depending on the molecular weight and the composition of the PLGA. These unique features allow different drug release profiles ranging from hours to several months. PLGA is enzymatically hydrolyzed into lactic and glycolic acid and undergoes endogenous metabolism, so as to form carbon dioxide and water.

However, the hydrophobic properties of PLGA negatively influence bio-adhesive properties thereof. Several studies report that the low adhesion capacity of PLGA on mucosal membranes leads to rapid clearance and, consequently, inadequate drug efficacy. To this end, there is an unmet need for the development of novel biodegradable and bio-adhesive films, such as for use in the biomedical and pharmaceutical fields.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

In one aspect of the invention, there is provided a film comprising an array of vertically aligned mushroom-type structures, the film comprises a biodegradable polymer, wherein a ratio between a height dimension and a width dimension of the mushroom-type structures is between 2:1 and 5:1, and wherein the film is characterized by adhesiveness to a biological tissue.

In one embodiment, a density of the vertically aligned structures within the array is between $1.2 \cdot 10^3$ and $1.2 \cdot 10^6/$ $cm^2$.

In one embodiment, the biodegradable polymer is selected from the group consisting of a polyether, a polyester, a polydioxanone, a polyphosphoester, a polyurethane, and a polyamide or any mixture or a co-polymer thereof.

In one embodiment, a center-to-center distance between a pair of adjacent vertically aligned structures within the array is between 1.5 and 150 um.

In one embodiment, the film is characterized by tensile strength of at least 0.5 MPa.

In one embodiment, the adhesiveness is greater by at least 10%, compared to a control.

In one embodiment, at least one surface of the film is characterized by a water contact angle of at least 100°.

In one embodiment, the film comprises a polymeric layer in contact with the vertically aligned mushroom-type structures.

In one embodiment, at least a portion of the film comprises a pharmaceutically active ingredient.

In one embodiment, a w/w concentration of the pharmaceutically active ingredient within the film is between 5 and 50%.

In one embodiment, pharmaceutically active ingredient is characterized by a log P between 1 and 6.

In one embodiment, the pharmaceutically active ingredient comprises an azole-based compound.

In one embodiment, the film is characterized by a prolonged release time of the pharmaceutically active ingredient.

In one embodiment, the prolonged release time is greater by at least 10%, compared to a control.

In one embodiment, the biological tissue comprises a mucosal tissue.

In one embodiment, the polymer is further in contact with a substrate.

In one embodiment, the width dimension of the vertically aligned mushroom-type structures is between 1 and 100 um.

In another aspect, there is a method for administering an active ingredient to a subject, comprising contacting the film of the invention with a biological tissue of a subject, thereby administering the active ingredient to the subject.

In one embodiment, the biological tissue comprises a mucosal tissue, a dermal tissue, a muscle tissue, and a urinary bladder tissue or any combination thereof.

In another aspect, there is a method for preventing or treating a medical condition, comprising administering the film of the invention to a subject, thereby preventing or treating the medical condition.

In one embodiment, administering comprising contacting the film with a biological tissue of the subject.

In one embodiment, the biological tissue comprises a mucosal tissue, a dermal tissue, a muscle tissue, and a urinary bladder tissue or any combination thereof.

In one embodiment, administering is selected from the group consisting of oral administration, vaginal administration, rectal administration, ocular administration, nasal administration, topical administration and dermal administration, or any combination thereof.

In one embodiment, the oral administration comprises buccal administration, sublingual administration, or both.

In addition to the exemplary aspects and embodiments described above, further aspects and embodiments will become apparent by reference to the figures and by study of the following detailed description.

Exemplary embodiments are illustrated in referenced figures. Dimensions of components and features shown in the figures are generally chosen for convenience and clarity of presentation and are not necessarily shown to scale. The figures are listed below:

BRIEF DESCRIPTION OF THE DRAWINGS

FIGS. 9A-9B are HR-SEM micrographs of MMF (9Ai-iii) and MMF-CTZ50 (9Bi-iii) at different magnifications: (i) Top view, scale bar 500 um (ii) Inclined view, scale bar 100 μm, (iii) Top view, scale bar 50 μm.

FIGS. 13B-13C are bar graphs showing mucoadhesion profiles of FF-CTZ50 and MMF-CTZ50 on agar/mucin plates at pH 6.8 (13B) and at pH 5.5 (13C) as determined by the displacement method. Values are the mean±s.d. of five experiments; *P<0.05, P<0.01, *P<0.001. FIG. 13D is a bar graph showing maximal adhesion strength of FF-CTZ50 and MMF-CTZ50 samples tested at 1 N normal preload on agar/mucin substrate (pH 6.8 and pH 5.5). Values are the mean±s.d. of three experiments; **P<0.01. FF-CTZ50 represents a control.

DETAILED DESCRIPTION

Figure 1:
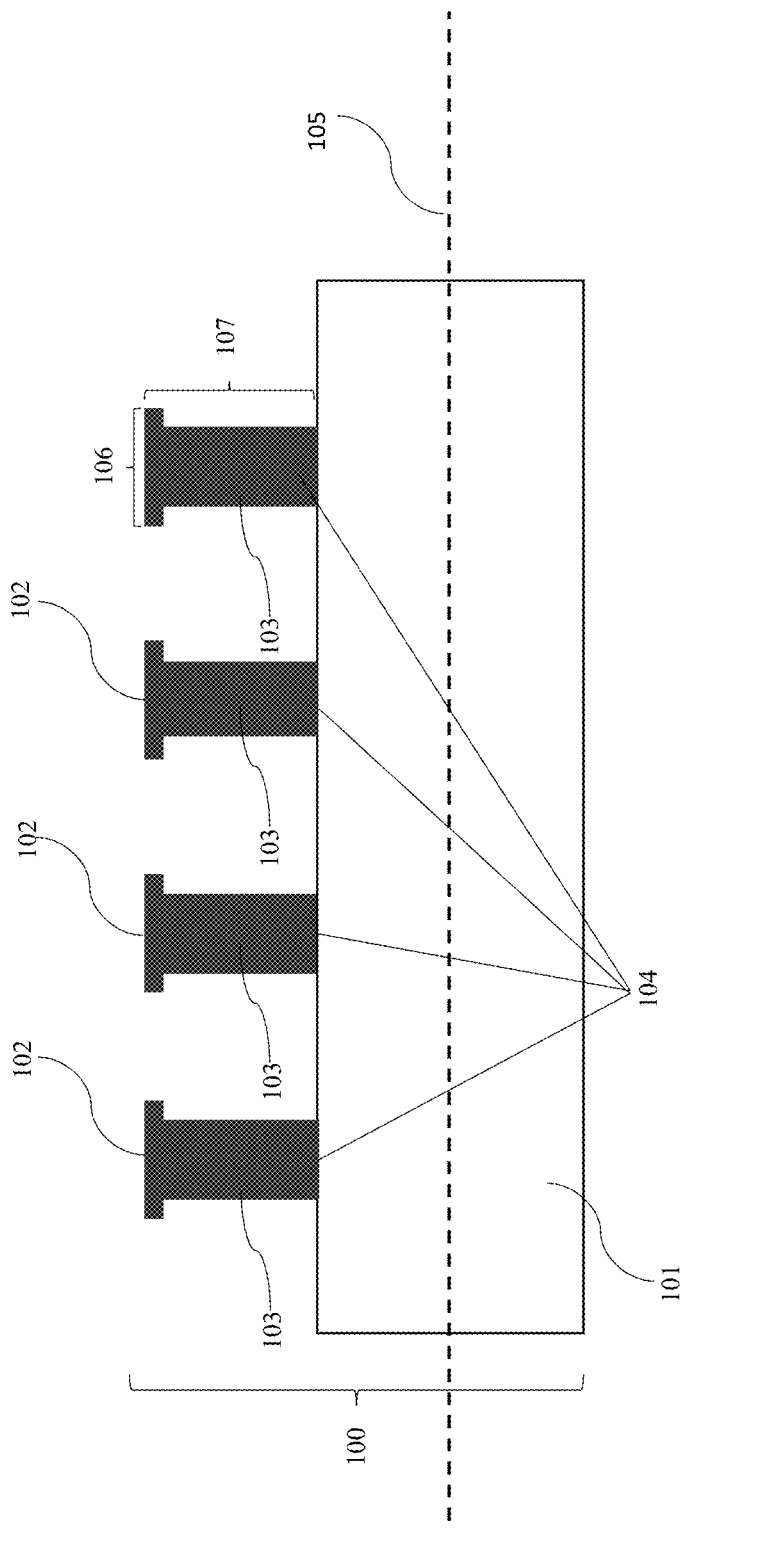
FIG. 1 shows a cross-section of an exemplary configuration of the article of the present disclosure, according to some embodiments of the present invention.

Disclosed herein are an article (e.g. a film) and a method for applying thereof to a target site of a subject, wherein the article is characterized by an adhesion property to the target site, and wherein the article is at least partially biodegradable. In some embodiments, the present article is characterized by muco-adhesiveness. In some embodiments, the present article is particularly useful in the treatment of medical conditions associated with mucosal tissue, such as oral and/or nasal cavity. In some embodiments, the present article is for mucous delivery of a biologically active agent.

Film

According to one aspect of the present invention, there is a film comprising an array of vertically aligned structures, wherein the film comprises a biodegradable material (e.g., a biodegradable polymer), wherein a diameter of any one of the vertically aligned structures is between 1 and 100 μm, and wherein the film is characterized by adhesiveness to a biological tissue.

According to one aspect of the present invention, there is an article comprising a polymeric layer, wherein a surface of the polymeric layer comprises an array of vertically aligned structures, wherein a diameter of the vertically aligned structures is between 1 and 100 μm, and wherein the surface is characterized by adhesiveness to a biological tissue. In some embodiments, the article is at least partially biodegradable. In some embodiments, the surface of the polymeric layer comprises an array of vertically aligned structures.

In some embodiments, the article of the invention comprises a bottom layer comprising or in contact with an array of vertically aligned structures, wherein a ratio between a height dimension and a width dimension of the vertically aligned structures is between 2:1 and 5:1, wherein the surface is characterized by adhesiveness to a biological tissue, and wherein the article comprises a biodegradable material. In some embodiments, a diameter of the vertically aligned structures is between 1 and 100 μm.

In some embodiments, the article is in a form of a film. In some embodiments, the film is at least partially biodegradable and/or biocompatible film. In some embodiments, the article is in a form of a solid film. In some embodiments, the article is in a form of a patch. In some embodiments, the term "article" and the term "film," are used herein interchangeably. In some embodiments, the film is in a solid state. In some embodiments, the film is substantially devoid of a semi-solid or semi liquid (e.g. a gel). In some embodiments, the film is an adhesive film. In some embodiments, the film is a bio adhesive film.

In some embodiments, the film comprises a matrix. In some embodiments, the matrix comprises a biodegradable material. In some embodiments, the matrix is formed by the biodegradable material. In some embodiments, the matrix consists essentially of the biodegradable material. In some embodiments, the matrix is a polymeric matrix.

In some embodiments, the biodegradable material comprises a biodegradable polymer. In some embodiments, the biodegradable material is a biodegradable polymer. In some embodiments, at least 70%, at least 80%, at least 90%, at least 95%, at least 99%, at least 99.9% by weight of the matrix consists of a biodegradable polymer.

In some embodiments, the matrix is a polymeric matrix. In some embodiments, the film comprises a polymeric matrix. In some embodiments, the film comprises a polymeric biodegradable matrix. In some embodiments, the film comprises a polymeric adhesive matrix. In some embodiments, the film comprises a polymeric mucoadhesive matrix. In some embodiments, the film comprises a polymeric biodegradable mucoadhesive matrix.

In some embodiments, the film comprises a first adhesive surface and a second surface. In some embodiments, the second surface is substantially non-adhesive. In some embodiments, the second surface is devoid of adhesiveness. As used herein the term "adhesive" refers to adhesiveness of the biodegradable film or a part thereof to a biological tissue.

As used herein, the term "biological tissue" refer to any surface comprising cells and/or biological molecules (e.g. proteins, polysaccharides, lipids, nucleic acids).

In some embodiments, the film is in a form of a layer. In some embodiments, the film comprises one more layers. In some embodiments, the film comprises a bottom layer and a top layer. In some embodiments, the bottom layer and the top layer are biodegradable. In some embodiments, any one of the bottom layer and the top layer comprises a biodegradable polymer.

In some embodiments, the term "layer", refers to a substantially homogeneous substance of substantially uniform-thickness. In some embodiments, the term "layer", refers to a polymeric layer.

In some embodiments, the film (or matrix) is in a form of a polymeric layer in contact with or bound to the vertically aligned structures. In some embodiments, at least 70%, at least 80%, at least 90%, at least 95%, at least 99%, at least 99.9% by weight of the polymeric layer is biodegradable.

In some embodiments, the polymeric layer defines the bottom layer, and the vertically aligned structures define the top layer. In some embodiments, at least 70%, at least 80%, at least 90%, at least 95%, at least 99%, at least 99.9% by weight of the top layer is biodegradable. In some embodiments, the polymeric layer and/or the top layer comprises a biodegradable polymer. In some embodiments, the polymeric layer and/or the top layer consists essentially of a biodegradable polymer.

In some embodiments, the film comprises the polymeric layer in contact with the vertically aligned structures. In some embodiments, the vertically aligned structures are stably bound to the polymeric layer. In some embodiments, the vertically aligned structures and the polymeric layer are fused or molten together. In some embodiments, the vertically aligned structures are joined with the polymeric layer. In some embodiments, the vertically aligned structures are stably bound or linked to the polymeric layer, so as to result in a homogenous biodegradable film.

In some embodiments, bound is via a non-covalent bond (e.g. electrostatic interaction, van-der-Waals bond, dipole-dipole interactions, hydrogen bond, London forces or any combination thereof). In some embodiments, bound is via a covalent bond. The terms "covalent bond" and "non-covalent bond" are well-understood by a skilled artisan.

In some embodiments, the first adhesive surface is in a form of a plurality of vertically aligned structures. In some embodiments, the first adhesive surface comprises a plurality of vertically aligned structures. In some embodiments, the adhesiveness property of the film (e.g. of the first adhesive surface) is predetermined by the plurality of vertically aligned structures. In some embodiments, the second surface of the film comprises a plurality of vertically aligned structures. In some embodiments, the second surface of the film is characterized by adhesiveness to a biological tissue.

In some embodiments, the film comprises one or more biodegradable polymer. In some embodiments, the biodegradable polymer is a single polymer or different polymers. In some embodiments, the film consists substantially of a single biodegradable polymer. In some embodiments, the polymeric layer and vertically aligned structures are composed of the same biodegradable polymer. In some embodiments, the polymeric layer and vertically aligned structures consist essentially of the same biodegradable polymer. In some embodiments, a biodegradable polymer of the polymeric layer and a biodegradable polymer of the vertically aligned structures are different biodegradable polymers.

In some embodiments, the polymeric layer and the vertically aligned structures are characterized by the same degradation rate. In some embodiments, the polymeric layer and the vertically aligned structures are characterized by different degradation rates. One skilled in the art will appreciate, that the degradation rate may be predetermined by the chemical composition, and/or by the geometrical shape or dimension of the polymeric layer and of the vertically aligned structures.

In some embodiments, the degradation rate of the article is predetermined by the chemical composition, average molecular weight (MW), and/or the structure (e.g. branched versus linear polymer; block co-polymer versus graft co-polymer; number of blocks and/or MW of any one of the blocks) of the biodegradable polymer.

In some embodiments, the biodegradable polymer comprises a block-copolymer. In some embodiments, the degradation rate is predetermined by the weight ratio between the blocks of the block-copolymer.

In some embodiments, the degradation rate of the biodegradable polymer and/or the article comprising thereof, is predetermined by the weight ratio between the blocks of the co-polymer, or by the weight ratio between the polymers composing the biodegradable polymer.

In some embodiments, the degradation rate of the biodegradable polymer is controllable by varying the chemical composition of the biodegradable polymer (e.g. by varying the polymers within the mixture of polymers, and/or by varying the ratio between the polymeric blocks within the block- and/or graft-copolymer). In some embodiments, the degradation rate of the article (or of the film of the invention) is controllable by adding a non-degradable polymer, or a non-degradable particle (such as a metal oxide particle) to the biodegradable polymer. One skilled in the art will appreciate, that by controlling or adjusting the degradation rate of the biodegradable polymer and/or of the article comprising thereof, the adhesive strength and/or release rate may be affected. In some embodiments, the degradation rate of the biodegradable polymer and/or the article comprising thereof, predetermines (e.g. increases or decreases by at least 10%) the release rate of an active agent form the article of the invention. In some embodiments, the degradation rate of the biodegradable polymer and/or the article comprising thereof, predetermines (e.g. increases or decreases by at least 10%) the adhesive strength of the article of the invention.

In some embodiments, a w/w ratio of the non-degradable polymer and/or a non-degradable particle within the film of the invention is between 0.1 and 50%, between 0.1 and 1%, between 1 and 5%, between 5 and 10%, between 10 and 20%, between 20 and 50%, including nay range therebetween.

In some embodiments, the film of the invention comprises a non-biodegradable polymer. In some embodiments, the terms "non-degradable" and "non-biodegradable" are used herein interchangeably.

In some embodiments, the film of the invention comprises a biocompatible polymer. Non-limiting examples of non-degradable polymers include but not limited to a polysiloxane (e.g. PDMS); a polyamide (e.g. nylon); a polysulfone; a polyether ether ketone (PEEK); a polyacrylate, a poly-methacrylate, a polyacrylate ester (e.g., poly(methyl methacrylate), poly(ethyl methacrylate), poly(methyl acrylate) and poly(ethyl acrylate)); including any copolymer thereof (including any ratio of the respective monomers) and/or any combination thereof.

As used herein, the term "biocompatible", is intended to describe materials that, are non-toxic to cells in vitro and upon administration in vivo, do not induce undesirable long-term effects.

As used herein, the term "biodegradable", is intended to describe materials comprising covalent bonds that are degraded in vivo, wherein the degradation of the covalent bond occurs inter alia via hydrolysis, and/or via an enzymatic reaction. Further, the term "biodegradable", as used herein, encompass bioerodible (and optionally biocompatible) polymers, which are well-known in the art. The hydrolysis can involve a direct reaction with an aqueous medium or can be catalyzed chemically or enzymatically. "Aqueous medium" refers to water, aqueous solutions, physiological media or biological fluids (e.g., body fluids), and other pharmaceutically acceptable media. Suitable hydrolysable covalent bonds are selected from the group containing: esters, urethanes, carbamates, carbonates, ethers, azo linkages, anhydrides, thioesters, and combinations thereof.

Non-limiting examples of biodegradable polymers appropriate for forming the film of the invention include but are not limited to: polyethers (e.g. polyethyleneglycol (PEG)), polyesters (e.g. poly-l-lactide (PLLA), poly-d-l-lactide (PLA), a polyglycolide (PGA), and/or any salt, co-polymer and/or a combination and/or a mixture thereof), polycaprolactones, polyhydroxybutyrate, polyhydroxyvalerate), polydioxanones, polyurethanes, polyphosphoesters, polyurethanes, and polyamides (e.g. polyamino acids) including any salt, any co-polymer or any combination thereof.

In some embodiments, the biodegradable polymer is selected from the group consisting of a polyether, a polyester, a polydioxanone, a polyphosphoester, a polyurethane, and a polyamide or any combination or a co-polymer thereof. In some embodiments, the biodegradable polymer comprises a mixture of polymers. In some embodiments, the biodegradable polymer comprises two or more polymers.

In some embodiments, the biodegradable polymer comprises or consists essentially of one or more polyester such as polylactide-co-polyglycolide (PLGA) including any derivatives (e.g., such as PLA, PGA and/or any salt thereof) and/or any copolymer thereof. In some embodiments, a w/w ratio between the polyglycolide (including any salt and polylactide within PLGA is between 10:1 and 1:10, between 10:1 and 8:1, between 8:1 and 6:1, between 6:1 and 4:1, between 4:1 and 2:1, between 2:1 and 1:1, between 1:1 and 1:2, between 1:2 and 1:4, between 1:4 and 1:6, between 1:6 and 1:8, between 1:8 and 1:10, including any range therebetween.

Reference is now made to FIG. 1, showing a cross-sectional view of an exemplary configuration of the article of the invention. Optionally, the article 100 comprises a polymeric layer 101. Optionally, the polymeric layer 101 is planar. Optionally, the polymeric layer 101 defines a plane. Optionally, the polymeric layer 101 is the bottom layer. Optionally, the polymeric layer 101 is curved and/or bent. Optionally, the polymeric layer 101 is shapeable or flexible, so as to allow variation of the article's dimension and/or geometric shape. Optionally, the polymeric layer 101 is substantially biodegradable comprising one or more biodegradable polymers.

Optionally, the polymeric layer 101 comprises a plurality of vertically aligned structures 104 bound or linked thereto. Optionally, the plurality of vertically aligned structures 104 form an array on top of the polymeric layer 101. Optionally, the article 100 comprises a polymeric layer 101 in contact with or bound to the array of vertically aligned structures 104. Optionally, the plurality of vertically aligned structures 104 are arranged in rows, wherein the rows are optionally parallel to a longitudinal axis 105 of the article. Optionally, the plurality of vertically aligned structures 104 is arranged along the longitudinal axis 105 of the article. Optionally, the plurality of vertically aligned structures 104 is configured to provide adhesiveness to a biological tissue, as described herein.

In some embodiments, the vertically aligned structures are characterized by a random geometric form or shape. In some embodiments, the vertically aligned structures are characterized by a predefined geometric form or shape. In some embodiments, the vertically aligned structures are uniformly shaped. In some embodiments, a tri-dimensional shape of at least 80%, at least 85%, at least 90%, at least 95%, at least 97%, at least 99% of the vertically aligned structures is the same or different.

Optionally, the plurality of vertically aligned structures 104 is in a form of mushroom-type structures. Optionally, the plurality of vertically aligned structures 104 (e.g. mushroom-type structures) comprise a stem 103 and a cap 102. Optionally, the stem 103 and the cap 102 are bound or joined together, wherein bound and joined are as described herein. Optionally, the stem 103 is bound to the polymeric layer 101. Optionally, each of the plurality of vertically aligned structures 104 is bound to the polymeric layer 101 via the stem 103. Optionally, each of the plurality of vertically aligned structures 104 is characterized by a height dimension 107. Optionally, the cap 102 is characterized by a width dimension 106. Optionally, the width dimension (or cross-section) of the stem 103 is greater than the cross-section 106 of the cap 102. Optionally, the stem 103 has any three-dimensional shape. Optionally, the stem 103 has a cylindrical shape. Optionally, the stem 103 has a conical shape. Optionally, the cap 102 has any three-dimensional shape, for example being in a form of a circle, an ellipse, a sphere, a hemisphere, a cylinder, a rectangle, a triangle, a polygon, a prism, or any combination thereof.

As used herein, the term "cross-section" refers to a width dimension of the vertically aligned structure. In some embodiments, the cross-section and/or width dimension as used hereinthroughout refers to a transversal cross section which is parallel to the polymeric layer 101. In some embodiments, the cross-section is measured parallel to the longitudinal axis of the film. In some embodiments, the cross-section and/or width dimension is measured perpendicular to a longitudinal axis of the vertically aligned structure. In some embodiments, the terms "cross-section" and "width dimension" are used herein interchangeably. In some embodiments, the terms "height dimension" and "height" are used herein interchangeably. In some embodiments, the terms "width dimension" and "width" are used herein interchangeably.

In some embodiments, the cap and the stem are composed of different polymers (e.g. biodegradable polymers). In some embodiments, the cap and the stem are composed of the same polymer. In some embodiments, the cap and the stem independently comprise a biodegradable polymer.

In some embodiments, a ratio between the cross-section or width 106 of the cap 102 and the cross-section of the stem 103 within the mushroom-type structures is between 2:1 and 4:3, between 2:1 and 3:2, between 3:2 and 4:3, including any range therebetween.

In some embodiments, a cross-section (e.g., diameter) of the vertically aligned structures is between 1 and 100 μm, between 1 and 5 μm, between 5 and 10 μm, between 10 and 20 um, between 20 and 30 um, between 30 and 40 μm, between 40 and 50 um, between 50 and 60 um, between 60 and 70 um, between 70 and 80 um, between 80 and 100 um, including any range therebetween. In some embodiments, the cross-section relates to at least 50%, at least 60%, at least 70%, at least 80%, at least 90%, at least 95%, at least 97%, at least 99% of the vertically aligned structures.

In some embodiments, a cross-section (e.g., diameter) of the cap is between 1 and 100 um, between 1 and 5 um, between 5 and 10 um, between 10 and 20 um, between 20 and 30 um, between 30 and 40 um, between 40 and 50 um, between 50 and 60 um, between 60 and 70 um, between 70 and 80 um, between 80 and 100 um, including any range therebetween.

In some embodiments, a cross-section (e.g., diameter) of the stem is between 1 and um, between 1 and 5 um, between 5 and 10 um, between 10 and 20 um, between 20 and 30 um, between 30 and 40 um, between 40 and 50 um, between 50 and 60 um, between 60 and 70 um, between 70 and 80 um, including any range therebetween.

In some embodiments, a ratio between a height 107 and a cross-section (or width) of the vertically aligned structures is between 2:1 and 5:1, between 2:1 and 3:1, between 3:1 and 4:1, between 4:1 and 5:1, including any range therebetween.

In some embodiments, a ratio between a height of the vertically aligned structure (e.g., mushroom-type structure) and a cross-section (or diameter) of the cap is between 2:1 and 5:1, between 2:1 and 3:1, between 3:1 and 4:1, between 4:1 and 5:1, including any range therebetween.

In some embodiments, a ratio between a height of the stem and a cross-section (or diameter) of the cap is between 2:1 and 5:1, between 2:1 and 3:1, between 3:1 and 4:1, between 4:1 and 5:1, including any range therebetween.

In some embodiments, a height of the vertically aligned structures is between 1 and 10 um, between 10 and 20 um, between 10 and 50 um, between 50 and 100 um, between 100 and 200 um, between 200 and 300 um, between 300 and 400 um, between 400 and 500 um, between 500 and 600 um, between 600 and 700 um, between 700 and 900 um, including any range therebetween.

In some embodiments, the height of the vertically aligned structures refers to a length of the stem or to a length of the entire vertically aligned structure (e.g. a combined length of the stem and of the cap).

In some embodiments, a density of the vertically aligned structures on a surface of the film of the invention is between $1 \cdot 10^3$ and $1.5 \cdot 10^6/cm^2$, between $1 \cdot 10^3$ and $1 \cdot 10^4/cm^2$, between $1 \cdot 10^4$ and $1 \cdot 10^5/cm^2$, between $1 \cdot 10^5$ and $1 \cdot 10^6/cm^2$, between $1 \cdot 10^6$ and $1.5 \cdot 10^6/cm^2$, including any range therebetween.

In some embodiments, the term "density" refers to a number of vertically aligned structures per surface area of the film (e.g. within a square centimeter). In some embodiments, the density refers to a number of vertically aligned structures per surface area of the array. One skilled in the art will appreciate, that if the vertical structures are uniformly distributed on or within the film of the invention (e.g. on top of the polymeric layer), the density within the entire surface of the film is substantially the same. However, if the vertical structures are non-uniformly distributed on or within the film surface (such as forming distinct arrays of vertical structures), the density refers to the number of vertically aligned structures per surface area of the array.

In some embodiments, an outer surface of the cap is characterized by a surface roughness of between 0.1 and 100 um, between 0.1 and 1 um, between 1 and 10 um, between 10 and 50 um, between 50 and 100 um, including any range therebetween.

In some embodiments, a center-to-center distance between a pair of adjacent vertically aligned structures is between 1 and 150 um, between 1 and 5 um, between 5 and between 10 and 15 um, between 15 and 20 um, between 20 and 30 um, between 30 and 50 um, between 50 and 70 um, between 70 and 90 um, between 90 and 100 um, between 100 and 150 um, between 150 and 200 um, between 200 and 300 um, between 300 and 400 um, between 400 and 500 um, including any range therebetween.

In some embodiments, a center-to-center distance refers to a distance between adjacent vertically aligned structures within the array.

In some embodiments, the film of the invention is characterized by a mechanical stability. As used herein the term "stability" refers to the capability of the film of the invention to maintain its structural and/or mechanical integrity. In some embodiments, the article is referred to as stable, if the article is characterized by a mechanical integrity sufficient to maintain the position and/or the vertical alignment of any one of the plurality of vertically aligned structures. In some embodiments, the stable film or article substantially maintains its adhesiveness to the biological tissue. In some embodiments, the stable film or article is applicable to a target site of the subject. In some embodiments, the stable film or article maintain its structural and/or mechanical integrity at the target site for at least 1 h, at least 2 h, at least 3 h, at least 5 h, including any range between.

In some embodiments, the stable film or article is rigid under operable conditions. In some embodiments, the stable film is inert to the operable conditions. The operable conditions may be referred to physiological conditions, such as physiological conditions of a mucosal and/or dermal tissue (e.g. oral and/or nasal cavity) such as pH, moisture, enzymatic species, and temperature or any combination thereof).

In some embodiments, the film of the invention (e.g., a mechanically stable film) is characterized by a tensile strength of at least 0.5 MPa. In some embodiments, the film of the invention is characterized by a tensile strength of between 0.5 and 100 MPa, between 0.5 and 1 MPa, between 1 and 10 MPa, between 10 and 50 MPa, between 50 and 100 Mpa, including any range between.

In some embodiments, the adhesive surface of the film is characterized by a water contact angle of at least 100°. In some embodiments, the first adhesive surface of the film is characterized by a water contact angle of at least 100°, at least 110°, at least 120°, at least 130°, at least 140°, at least 150°, including any range therebetween.

As used herein, the term "vertically aligned structures" does not necessarily refer to perpendicular alignment of the structures. In some embodiments, the vertically aligned structures are substantially perpendicular to the plane of the polymeric layer 101, wherein substantially is as described herein. In some embodiments, the vertically aligned structures are lateral to the plane of the polymeric layer. In some embodiments, at least a portion of the vertically aligned structures has an angle of between 70 and 120°, between 70 and 80°, between 80 and 90°, between 90 and 100°, between 100 and 120° relative to the plane of the polymeric layer including any range therebetween.

The term "array" does not necessarily refer to any specific geometric arrangement of the vertically aligned structures. In some embodiments, the vertically aligned structures are devoid of any specific pattern. In some embodiments, the vertically aligned structures are randomly distributed on top of the polymeric layer.

In some embodiments, the vertically aligned structures are in a form of patterned structures. In some embodiments, the vertically aligned structures are characterized by a pattern. In some embodiments, the vertically aligned structures define a patterned array.

In some embodiments, the array is in a form of a single row, or a plurality of rows, which may be parallel. In some embodiments, the array is linear or curved. In some embodiments, the plurality of vertically aligned structures are arranged on the polymeric layer in a form of two or more parallel rows, so as to form parallel arrays.

In some embodiments, the vertically aligned structures are arrayed in one or more of a circular array, an oval array, a rectangular array, a triangular array, a polygon array, a columnar array, and/or a horseshoe array. In some embodiments, the array defines an axis (e.g. a longitudinal axis) of the substrate. In some embodiments, the vertically aligned structures are arranged along an axis of the polymeric layer.

Optionally, the plurality of vertically aligned structures 104 are positioned on or within the polymeric layer 101, so as to result in a sufficient adhesiveness described herein. Optionally, the first adhesive surface comprises the plurality of vertically aligned structures 104, wherein a density of the vertically aligned structures is sufficient for inducing adhesiveness of the biodegradable film to a biological tissue.

Figure 2:
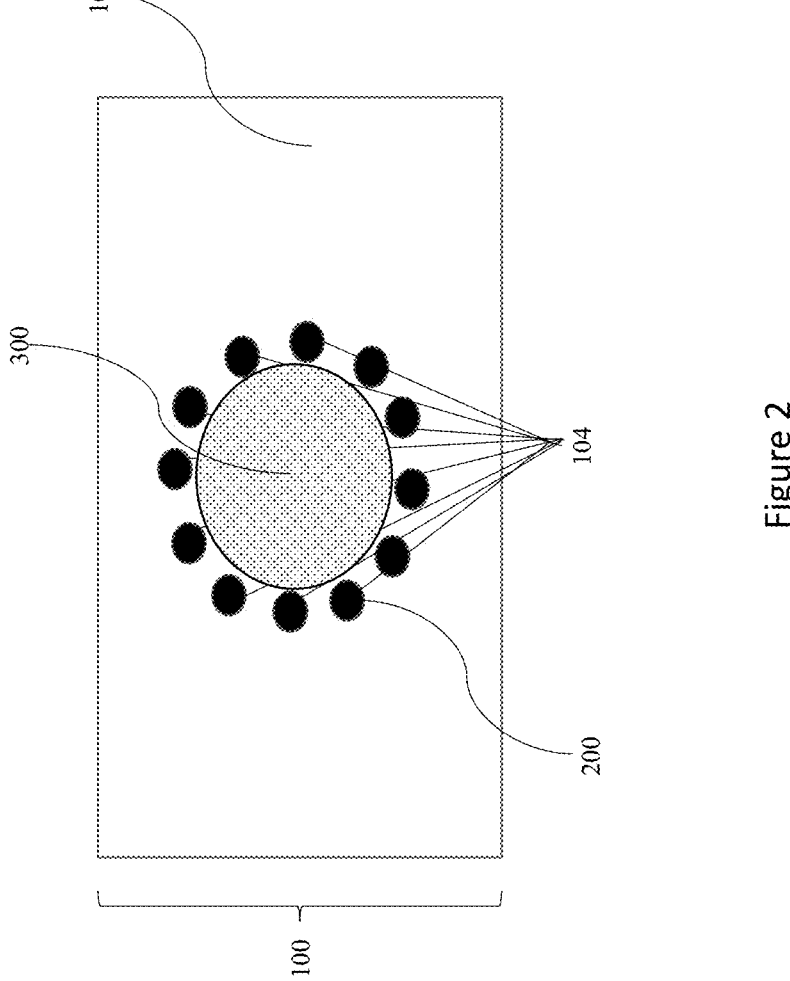
FIG. 2 shows top view of an exemplary configuration of the article of the present disclosure, according to some embodiments of the present invention.

Reference is now made to FIG. 2, showing a top view of an exemplary configuration of the article of the invention. Optionally, the article 100 comprises the polymeric layer 101, wherein at least a portion of the polymeric layer comprises or is bound to the array of vertically aligned structures 104. Optionally, the array 104 may obtain any geometrical form. Optionally, the array 104 is in a form of a circle. Optionally, the array 104 is in a form of an ellipse. Optionally, the array 104 has a rectangular form. Optionally, a portion 200 of the polymeric layer comprises an array of vertically aligned structures 104. Optionally, the portion 200 of the polymeric layer is adhesive. Optionally, a portion 300 of the polymeric layer is devoid of vertically aligned structures 104. Optionally, a portion 300 of the polymeric layer is devoid of adhesiveness. Optionally, the article 100 is in a form of a patch. Optionally, the article 100 is configured to adhere to and/or around a perimeter of an injury on or within a biological tissue.

In some embodiments, the outer layer of the article (and/or the film of the invention) is characterized by adhesiveness to a biological tissue. In some embodiments, the outer layer of the article (and/or the film of the invention) is characterized by adhesiveness to a mucosal tissue. In some embodiments, the biological tissue is a wet tissue. In some embodiments, the biological tissue comprises a mucous membrane. In some embodiments, the film of the invention is characterized by sufficient adhesiveness to the biological tissue, so as to retain at the application site for at least 1 h, at least 2 h, at least 3 h, at least 5 h, at least 10 h, at least at least 20 h, at least 25 h, at least 2d, at least 3d, at least 4d, at least 5d, at least 7d, at least 9d, at least 15d, at least 20d, at least 30d, including any range between.

In some embodiments, the outer layer of the article (and/or the film of the invention) is substantially devoid of a tacky substance (such as a glue). In some embodiments, film of the invention consists essentially of the biodegradable polymer and optionally of the active agent (e.g., a drug). In some embodiments, the film of the invention is substantially devoid of a non-biodegradable polymer, or a non-biocompatible polymer.

In some embodiments, the term "adhesiveness" or the term "sufficient adhesiveness" (which are used herein interchangeably) refers to the ability of the film and/or article of the invention to form a stable bond (e.g., non-covalent, or physical interaction) to at least one surface of the biological tissue. Thus, term adhesiveness is well known in the art, an may be related to physical forces (bonds or interactions, including dipole-dipole interactions, hydrogen bonds, London forces, Van-der-Waals forces, or any physical forces such as vacuum, capillary forces, etc.) that exists in the area of contact between two surfaces (e.g. the outer surface of the film of the invention and the outer surface of the biological tissue), holding them together.

In some embodiments, a stable bond is capable of retaining the film and/or article of the invention at the application site (e.g. bound to the biological tissue) for at least 1 h, at least 2 h, at least 3 h, at least 5 h, at least 10 h, at least 15 h, at least 20 h, at least 25 h, at least 2d, at least 3d, at least 4d, at least 5d, at least 7d, at least 9d, at least 15d, at least 20d, at least 30d, including any range between. In some embodiments, the term "adhesiveness" refers to adhesive strength of the film and/or article of the invention, as described hereinbelow.

In some embodiments, the article comprises an adhesive outer layer. In some embodiments, the adhesive outer layer is configured to adhere to a tissue of a subject (e.g., at an application site). In some embodiments, the outer layer of the article (and/or the film of the invention) has adhesiveness sufficient so as to retain the article at the application site for at least 1 h, at least 2 h, at least 3 h, at least 5 h, at least 10 h, at least 15 h, at least 20 h, at least 25 h, at least 2d, at least 3d, at least 4d, at least 5d, at least 7d, at least 9d, at least 15d, at least 20d, at least 30d, including any range between.

In some embodiments, the film of the invention is between 1 μm and 5 mm thick. In some embodiments, the composition is characterized by a thickness from 1 to 10 μm, from 10 to 20 μm, from 20 to 30 μm, from 30 to 40 μm, from 40 to 50 μm, from 50 to 100 μm, from 100 to 150 μm, from 150 to 200 μm, from 200 to 300 μm, from 300 to 400 μm, from 400 to 500 μm, from 500 to 600 μm, from 600 to 700 μm, from 700 to 800 μm, from 800 to 900 μm, from 900 to 1000 μm, from 1000 to 2000 μm, from 2000 to 3000 μm, from 3000 to 4000 μm, from 4000 to 5000 μm, including any range or value therebetween.

In some embodiments, the terms "thick" or "thickness" including any grammatical form thereof, refer to an average thickness.

In some embodiments, the film of the invention is characterized by an adhesion strength of at least 30 KPa, at least 40 KPa, at least 50 KPa, at least 60 KPa, at least 70 KPa, at least 80 KPa, at least 90 KPa, at least 100 KPa, at least 200 KPa, including any range therebetween, wherein the adhesion strength is measured according to an adhesion test (e.g. under wet conditions, as described herein). The adhesion test is as described hereinbelow.

In some embodiments, the article is characterized by an enhanced adhesion to a wet biological tissue. In some embodiments, enhanced comprises at least at least 20%, at least 50%, at least 60%, at least 70%, at least 80%, at least 90%, at least 95%, at least 97%, at least 99%, at least 200%, at least 300%, at least 400%, at least 500% greater adhesion, compared to a control. In some embodiments, the control comprises a film having the same chemical composition and being devoid of the plurality of vertically aligned structures.

In some embodiments, the vertically aligned structures (e.g. patterned in an array) induce adhesion of the film to the biological tissue. In some embodiments, the vertically aligned structures having a mushroom-type shape, a dimension (e.g. height, diameter and distance) and optionally arranged in an array as described herein, provide adhesiveness to a surface of the film. One skilled in the art will appreciate, that the adhesion strength of the film of the invention is unrelated to a presence of any adhesive excipient or adjuvant within the film.

In some embodiments, the film of the invention comprising the vertically aligned structures, as described herein is characterized by an enhanced adhesion strength, compared to a control, wherein enhanced is as described herein. In some embodiments, the control is the film having the same composition and being devoid of the vertically aligned structures. A comparison of the adhesion strength between the film of the invention and the control is demonstrated in the Example section.

In some embodiments, the article provides for a flexible patch-like substrate configured for external application at a body site. In some embodiments, the article is for the treatment or for the delivery of an active agent to the subject.

In some embodiments, the article of the invention is for application on top of an injury or damage of a biological tissue (e.g., a wound, an aphtha, a wart, an ulcer). In some embodiments, the biological tissue comprises a mucosal tissue, a dermal tissue, or both.

In some embodiments, the film is shapeable. In some embodiments, at least one dimension of the film is variable, e.g., by applying stress. In some embodiments, the film is shapeable along at least one dimension, e.g., a length dimension, a width dimension, a radial dimension, a diagonal dimension, and the like. In some embodiments, the film may be shaped and/or elongated, e.g., by a user and/or a medical practitioner, to become elongated, wider, increased in diameter, and/or a combination thereof.

In some embodiments, the film is foldable. In some embodiments, the article is flexible. In some embodiments, the film is characterized by elasticity. In some embodiments, the film is characterized by elasticity and/or foldability sufficient for application of the article on one or more region of the tissue (e.g. mucous or dermal tissue).

In some embodiments, the film further comprises an additive (e.g. a coloring agent, a taste agent, etc.).

In some embodiments, the film further comprises an active agent. In some embodiments, the active agent comprises a pharmaceutically active ingredient (e.g. a drug). In some embodiments, the film comprises a pharmaceutically effective amount of the active ingredient. In some embodiments, at least a portion of the film comprises a pharmaceutically active ingredient. In some embodiments, the pharmaceutically active ingredient is in contact with the film. In some embodiments, the pharmaceutically active ingredient is bound to the film. In some embodiments, the pharmaceutically active ingredient is embedded within the film. In some embodiments, the pharmaceutically active ingredient is homogenously mixed with the film. In some embodiments, the pharmaceutically active ingredient is homogenously dispersed within the film. In some embodiments, the pharmaceutically active ingredient is substantially located within the entire film. In some embodiments, the pharmaceutically active ingredient is located on top of the film. In some embodiments, the pharmaceutically active ingredient is incorporated on and/or within the film. In some embodiments, the pharmaceutically active ingredient and the film are in a form of a composite. In some embodiments, the pharmaceutically active ingredient is homogenously distributed within the film.

In some embodiments, the pharmaceutically active ingredient is in a form of a solid on and/or within the film. In some embodiments, the pharmaceutically active ingredient is in a form of an amorphous solid on and/or within the film. In some embodiments, the pharmaceutically active ingredient is in a form of a crystal on and/or within the film, wherein crystal includes any polymorphous form of the pharmaceutically active ingredient.

In some embodiments, the pharmaceutically active ingredient is non-homogenously distributed within the film. In some embodiments, the pharmaceutically active ingredient is substantially located on or within the cap, the stem, or the polymeric layer of the film including any combination thereof.

In some embodiments, the film is configured to encapsulate the active agent at a w/w concentration between 0.1 and 50%, is between 0.1 and 1%, is between 1 and 5%, is between 5 and 10%, is between 10 and 15%, is between 15 and 20%, is between 20 and 30%, is between 30 and 40%, is between 40 and 50% by total weight of the film, including any range therebetween.

In some embodiments, the film encapsulating the active agent is characterized by an enhanced adhesion to a wet biological tissue, as compared to a control (e.g. a similar film devoid of the active agent). In some embodiments, enhanced comprises at least at least 20%, at least 50%, at least 60%, at least 70%, at least 80%, at least 90%, at least 95%, at least 97%, at least 99%, at least 200%, at least 300%, at least 400%, at least 500% greater adhesion, compared to a control.

In some embodiments, the active agent comprises a food-additive (e.g., a nutraceutical). In some embodiments, the active agent comprises a drug (or a pharmaceutically active agent). In some embodiments, the drug is or comprises a fungicide, an anti-inflammatory agent (e.g., a steroid, NSAID), an analgesic, an anti-cancer drug, or any combination thereof. Additional drugs or pharmaceutically active agents are known in the art.

In some embodiments, the drug is characterized by a log P of between 1 and 6, between 1 and 2, between 2 and 4, between 4 and 6, including any range therebetween.

In some embodiments, the pharmaceutically active ingredient comprises an azole-based compound.

Non-limiting examples of azole-based compounds include but are not limited to: clotrimazole, itraconazole, ketoconazole, fluconazole, voriconazole, posaconazole and ravuconazole, including any derivative or any combination thereof.

In some embodiments, the film of the invention is configured to substantially release the active agent. In some embodiments, the film of the invention is configured to substantially release the active agent under physiological conditions (e.g. a temperature of about 36 C, a pH between 5 and 8, exposure to bodily fluids (e.g. saliva), and exposure to a tissue of a subject, such as a wet tissue). In some embodiments, the film of the invention is configured to substantially release the active agent upon contact thereof with a mucosal tissue. In some embodiments, the film of the invention is configured to release at least 50%, at least 60%, at least 70%, at least 80%, at least 90%, at least 93%, at least 95%, at least 97%, at least 99% by weight of pharmaceutically active ingredient including any range between, within a predetermined time period, wherein pharmaceutically active ingredient refers to the initial amount of the pharmaceutically active ingredient within the film. In some embodiments, the predetermined time period is as described herein. In some embodiments, the film is configured to release the pharmaceutically active ingredient due to at least partially degradation and/or erosion of the film. In some embodiments, the film of the invention is characterized by a gradual release profile of the pharmaceutically active ingredient (e.g. into the tissue and/or into a location adjacent to the application site).

In some embodiments, the film of the invention is configured to substantially release the active agent within a predetermined time period ranging between 1 h and 20 days (d), between 1 and 10 h, between 10 and 24 h, between 1 and 20d, between 1 and 5d, between 1 and 10d, between 1 and 8d, between 8 and 20d, between 1 and 15d, between 5 and 10d, between 10 and 15d, between 15 and 20d, including any range between.

In some embodiments, the film is characterized by a prolonged release time of the active agent, compared to a control. In some embodiments, prolonged comprise at least 20%, at least 50%, at least 60%, at least 70%, at least 80%, at least 90%, at least 95%, at least 97%, at least 99%, at least 200%, at least 300%, at least 400%, at least 500% greater release time, compared to a control.

In some embodiments, the film is characterized by a sustained release profile of the active agent (e.g. pharmaceutically active ingredient). An exemplary release profile is demonstrated in the Examples section.

In some embodiments, the film is substantially devoid of a nano-particulate matter. In some embodiments, the film is substantially devoid of biodegradable nano-particles. In some embodiments, the film is substantially devoid of an encapsulated active ingredient.

In some embodiments, the film is substantially devoid of an excipient. In some embodiments, the film is substantially devoid of an adhesive excipient (such as binder, tackifier, etc.). In some embodiments, the film is substantially devoid of an additional adhesive polymer (such as a polysaccharide, a peptide, a protein etc.).

In some embodiments, the film (e.g., the adhesive surface) is further in contact with or bound (e.g., adhered) to a substrate. In some embodiments, the substrate is in a form of capping and/or protecting layer. In some embodiments, the substrate is in a barrier layer, configured for preventing undesired adhesion of the film. In some embodiments, the substrate is configured for preventing adsorption of particles (e.g. dust, moisture, or any other contamination) on top of the film. In some embodiments, the substrate comprises a packaging material. In some embodiments, the substrate comprises a polymeric material. In some embodiments, the substrate comprises a thermoplastic polymer.

In some embodiments, the substrate comprises a polymer is selected from the group comprising: polytetrafluoroethylene, a fluorinated polyolefin, polyvinyl fluoride, polyethylene terephthalate (PET), polycyclohexylenedimethylene terephthalate (PCT), polycyclohexylenedimethylene terephthalate (PCTG), polyethylene naphthalate (PEN), polytrimethylene terephthalate (PTT), polybutylene terephthalate (PBT), a polyether, polyethyleneglycol (PEG), polypropylene (PP), polyethylene (PE), polycarbonate, polycaprolactone (PCL), polylactic acid (PLA), polylactic-co-glycolic acid (PLGA), polyhydroxyethyl methacrylate (polyHEMA), and polyurethane, including any combination or a copolymer thereof.

Uses

In another aspect, there is provided a method for treating or preventing a condition associated with a tissue damage, the method comprises contacting (or applying) the film of the invention on top of a damaged tissue of a subject, thereby obtaining the film stably bound to the damaged tissue. In some embodiments, stably bound is for a predetermined time period, as described herein. In some embodiments, the method is for sealing or adhering a damaged or injured tissue. In some embodiments, the damaged tissue a damaged mucosal tissue (such as oral and/or nasal cavity). In some embodiments, the method comprises contacting (or applying) the film of the invention on top of a damaged tissue of the subject, thereby adhering the film to the damaged tissue (e.g., to a lesion site).

In some embodiments, the damaged tissue comprises a medical condition associated with mucosal tissue. In some embodiments, the medical condition comprises a disease or disorder selected from the group consisting of fungal infection (e.g. candida infection of the mouth, throat, skin, nail and/or vagina), aphthous ulcer, pressure ulcer, a proliferative disease (e.g. oral cancer, bladder cancer, colon cancer), inflammatory bowel disease or a combination thereof. In some embodiments, the medical is a wound. In some embodiments, the damaged tissue comprises an injured tissue (e.g., a physical damage of the mucosal tissue).

According to another aspect of some embodiments of the present invention there is provided a method for administering an active agent to a subject, comprising contacting the film of the invention with a biological tissue of a subject, thereby administering the active agent to the subject. In some embodiments, the film of the invention comprises a pharmaceutically effective amount of the active agent.

In some embodiments, the biological tissue is as described herein. In some embodiments, the biological tissue is a moist tissue. In some embodiments, the biological tissue is as described herein. In some embodiments, the biological tissue is a substantially dry tissue (e.g. dermal tissue). In some embodiments, the biological tissue is a mucous and/or dermal tissue.

In some embodiments, contacting comprises providing the film and applying the film to a target site of the subject. In some embodiments, applying comprises contacting the adhesive surface with the target site (moist or dry) on or within the biological tissue or organ of the subject. In some embodiments, upon contacting the film with the biological tissue, the adhesive surface of the film faces or is bound to the biological tissue. In some embodiments, applying comprises pressing the film towards the biological tissue, so as to induce adhesion of the film thereto.

In some embodiments, the film or article of the invention is a medical device. In some embodiments, the medical device is an implantable medical device. In some embodiments, the medical device is for use in the field of general surgery, neurology, ear-nose and throat, urology, gynecology/obstetrics, thoracic, dental/maxillofacial, gastroenterology, plastic surgery, ophthalmology, cardiovascular and/or orthopedic medicine.

In some embodiments, the active agent is as described herein above. In some embodiments, the active agent comprises a food-supplementary ingredient. Other active agents are well-known in the art.

In some embodiments, the method is for administering a pharmaceutically effective amount of an active agent to the subject (e.g., to a target site on or within the mucosal tissue).

In some embodiments, the method is for locally administering an active agent. In some embodiments, the method is for topically administering the active agent. In some embodiments, the method is for mucosal administration (e.g. oral or nasal administration) of the active agent.

In some embodiments, administering is selected from the group consisting of oral administration, vaginal administration, rectal administration, ocular administration, nasal administration, topical administration and dermal administration, or any combination thereof. In some embodiments, oral administration comprises buccal administration, sublingual administration, or both.

In some embodiments, the method is for administering the active agent to the target site. In some embodiments, the target site is the application site of the film. In some embodiments, the method is for delivery of the active agent into a mucous or dermal tissue. In some embodiments, the method is for controlled delivery and/or release of the active agent into a mucous or dermal tissue of the subject.

In some embodiments, the method is for transmucosal and/or transdermal administration of the active agent. In some embodiments, the method is for sustained administration of the active agent. In some embodiments, the method is for sustained release of the active agent to the target site. In some embodiments, the method is for sustained release of the active agent to a biological tissue of the subject. In some embodiments, the biological tissue comprises a mucosal tissue, a dermal tissue, a muscle tissue, and a urinary bladder tissue or any combination thereof.

In some embodiments, the method is for sustained release of the active agent into an oral cavity. In some embodiments, administration and/or release comprises a pharmaceutically effective amount of the active agent.

According to another aspect of some embodiments of the present invention there is provided a method for preventing or treating a medical condition, comprising administering the film of the invention to a subject, thereby preventing, or treating the medical condition, wherein the film comprises a pharmaceutically effective amount of an active agent. In some embodiments, administering comprising contacting the film with a biological tissue of the subject, as described herein. In some embodiments, the biological tissue comprises a mucosal tissue, a dermal tissue, a muscle tissue, and a urinary bladder tissue or any combination thereof.

In some embodiments, administering comprises oral or nasal administration. In some embodiments, administering comprises topical administration. In some embodiments, administering comprises dermal administration. Other administration routes are as described hereinabove.

In some embodiments, the herein disclosed article is for treating a medical condition associated with mucosal tissue, such as oral and/or nasal cavity. In some embodiments, the medical condition comprises a disease or disorder selected from the group consisting of fungal infection (e.g. candida infection of the mouth, throat, skin, nail and/or vagina), aphthous ulcer, pressure ulcer, a proliferative disease (e.g. oral cancer, bladder cancer, colon cancer), inflammatory bowel disease or a combination thereof.

According to an aspect of embodiments of the invention there is provided a medicament comprising one or more films (or articles) disclosed herein and a pharmaceutically acceptable carrier.

According to some embodiments of the invention, the medicament is being packaged in a packaging material and identified in print, in or on the packaging material, for use in the treatment of a medical condition associated with any disease, medical condition, or disorder as described hereinthroughout.

In some embodiments, localized therapy in the oral cavity (i.e. inner oral tissue) is achieved within e.g., several hours of administration, e.g., topical administration. Without being bound by any particular mechanism, it is assumed that the mechanism of in release of the active agent from the disclosed film is likely to involve dissolution/erosion of the polymer.

In some embodiments, the disclosed film further comprises a labeling agent. As used herein, the phrase "labeling agent" or "labeling compound" describes a detectable moiety or a probe. The labeling agent may be attached to a portion of the polymer forming the film of the invention, directly or via a spacer. Alternatively, the labeling agent may be encapsulated within the void space within the polymeric film.

As used herein, the term "subject" refers to any animal (e.g., a mammal), including, but not limited to, humans, non-human primates, rodents, and the like, to which the compositions and methods of the present invention are administered. In some embodiments, the terms "subject" and "patient" are used interchangeably herein in reference to a human subject. In other embodiments, the terms "subject" and "patient" are used interchangeably herein in reference to a non-human subject.

General

As used herein the term "about" refers to ±10%. The terms "comprises", "comprising", "includes", "including", "having" and their conjugates mean "including but not limited to". The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

As used herein, the term "substantially" refers to at least 80%, at least 85%, at least 90%, at least 92%, at least 95%, at least 96%, at least 97%, at least 98%, at least 99%, including any range or value therebetween. Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

EXAMPLES

Reference is now made to the following examples which, together with the above descriptions, illustrate the invention in a non-limiting fashion.

Materials and Methods

Materials

PLGA-Purasorb (ID PDLG 5010 (50:50) with an inherent viscosity midpoint of 1 dl/g was donated by Corbion Purac (Gorinchem, the Netherlands). Organic solvents were purchased from Sigma Aldrich (Rehovot, Israel). PDMS sample with mushroom head surface texture purchased from Klettband Technik, Germany. Phosphate buffer saline was purchased from Hyclone Laboratories. Poly(vinylsiloxane) (PVS) was purchased from Coltene Whaledent AG (Altstatten, Switzerland).

PLGA Microstructures Preparation

Two samples made of PLGA were evaluated in a comparative study: (i) flat PLGA film (FF) used as a control reference, and (ii) PLGA film with biomimetic mushroom-type microstructures (MMF).

MMF samples were casted from the same PLGA material using a two-step molding technique. To do so, PVS negative templates were first prepared by replicating the pre-to-use mushroom-shaped microstructure made of PDMS with a cup diameter of 40 μm and areal density of 29000 elements per cm$^2$ [Art. 70140—Gecko® Nanoplast®]. This was purchased from "Klettband Technik" (Germany). Then, MMF samples were obtained by casting PLGA material into the negative templates made of PVS.

Figure 3:
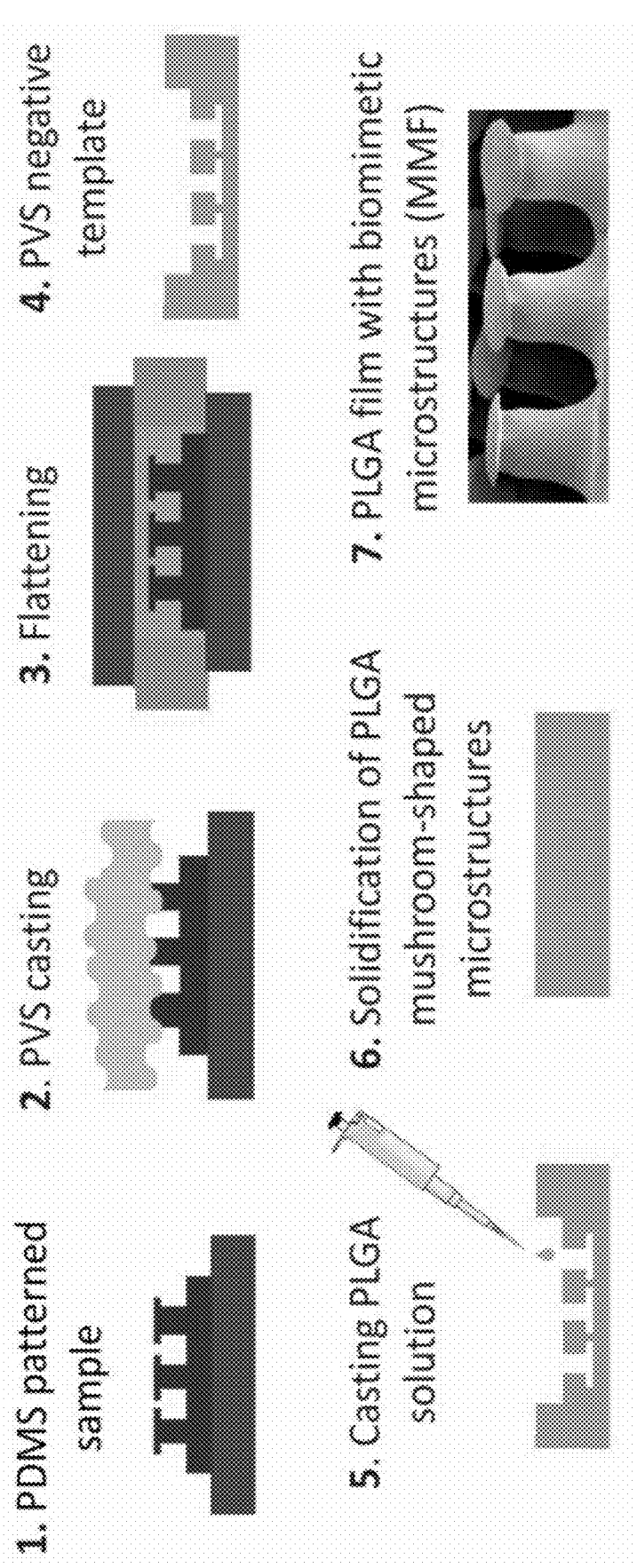
FIG. 3 shows a schematic illustration of a non-limiting exemplary preparation process of PLGA samples patterned with mushroom-type microstructures (MMF) (e.g. exemplary films of the invention) manufactured via a two-step molding technique.

The double replicating process consists of flattening the ready to use PDMS mushroom-shaped micro-structured film on a flat and rigid glass support covered with ethanol to avoid unwanted reaction between PDMS and PVS, then the PVS solution is applied on the patterned side to replicate the mushroom shape. Two spacers as well as a glass plate are used to unify the thickness of the PVS template. The template was released after PVS polymerization (about 10 min). The obtained PVS template was flattened on a rigid glass support. Afterwards, 25 mg of PLGA dissolved in 500 μL of chloroform (CHF) was cast into the PVS template and covered using drilled aluminum foil to prevent unwanted production of air bubbles due to fast solvent evaporation rate and high viscosity of the polymeric solution. Complete solidification of PLGA takes about 24 h, whereupon the obtained film with mushroom microstructure was removed. (See process illustration in FIG. 3). It is important to note that flat PLGA sample FF (used as a control reference) was obtained by flowing the same process method, however replicating the rigid flat glass instead of the mushroom-shaped microstructures.

Morphological Evaluation of Mushroom Microstructures

Figure 4B:
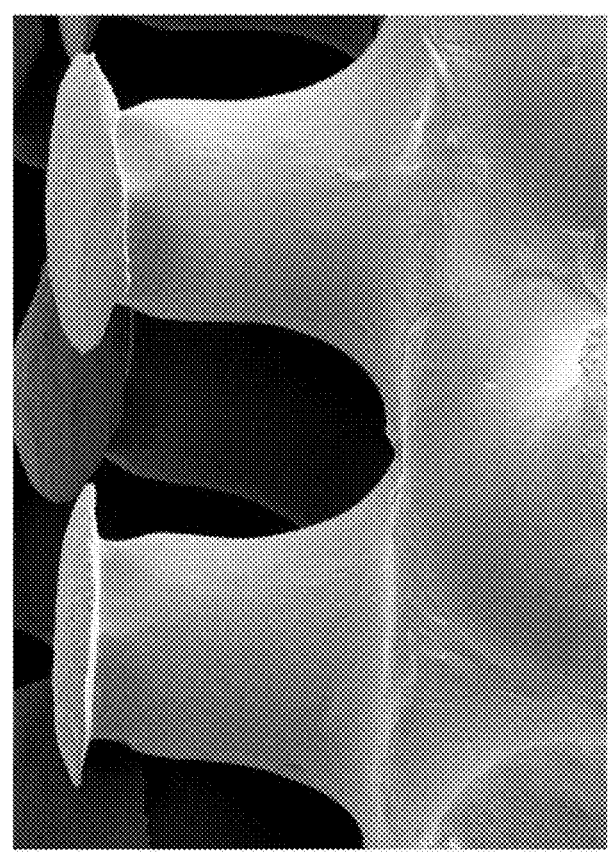
FIGS. 4A-4B are HR-SEM (high resolution scanning electron microscope) micrographs of the obtained PLGA mushroom-shaped microstructure (e.g. exemplary films of the invention), (4A) top view and (4B) side view.
Figure 4A:
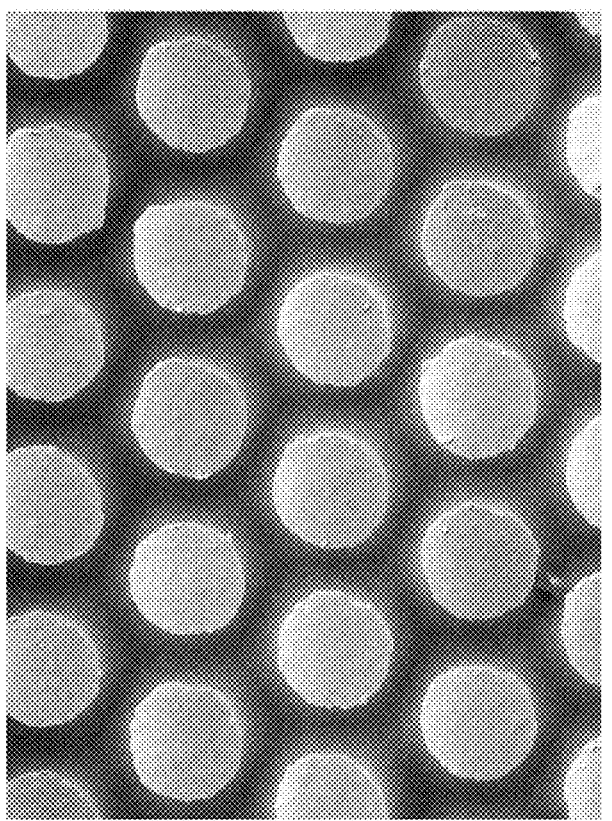

The morphology of the obtained MMF samples was characterized using an extreme high resolution scanning-electron microscope (XHR SEM) (model Magellan 400 L, FEI, Germany). Given that PLGA is electrically non-conductive, samples were extracted from the obtained film and coated with gold and 5% of palladium to produce a conductive and homogenous 5 nm thin layer on the surface, thus enabling SEM observation. It is important to assure that the coated sample are used only for HR-SEM observation and not for adhesion measurement. (exemplary HR-SEM images of the patterned surface of MMF samples are represented in FIGS. 4A and 4B)

PLGA Films Wettability by Contact Angle Measurement

Figure 5:
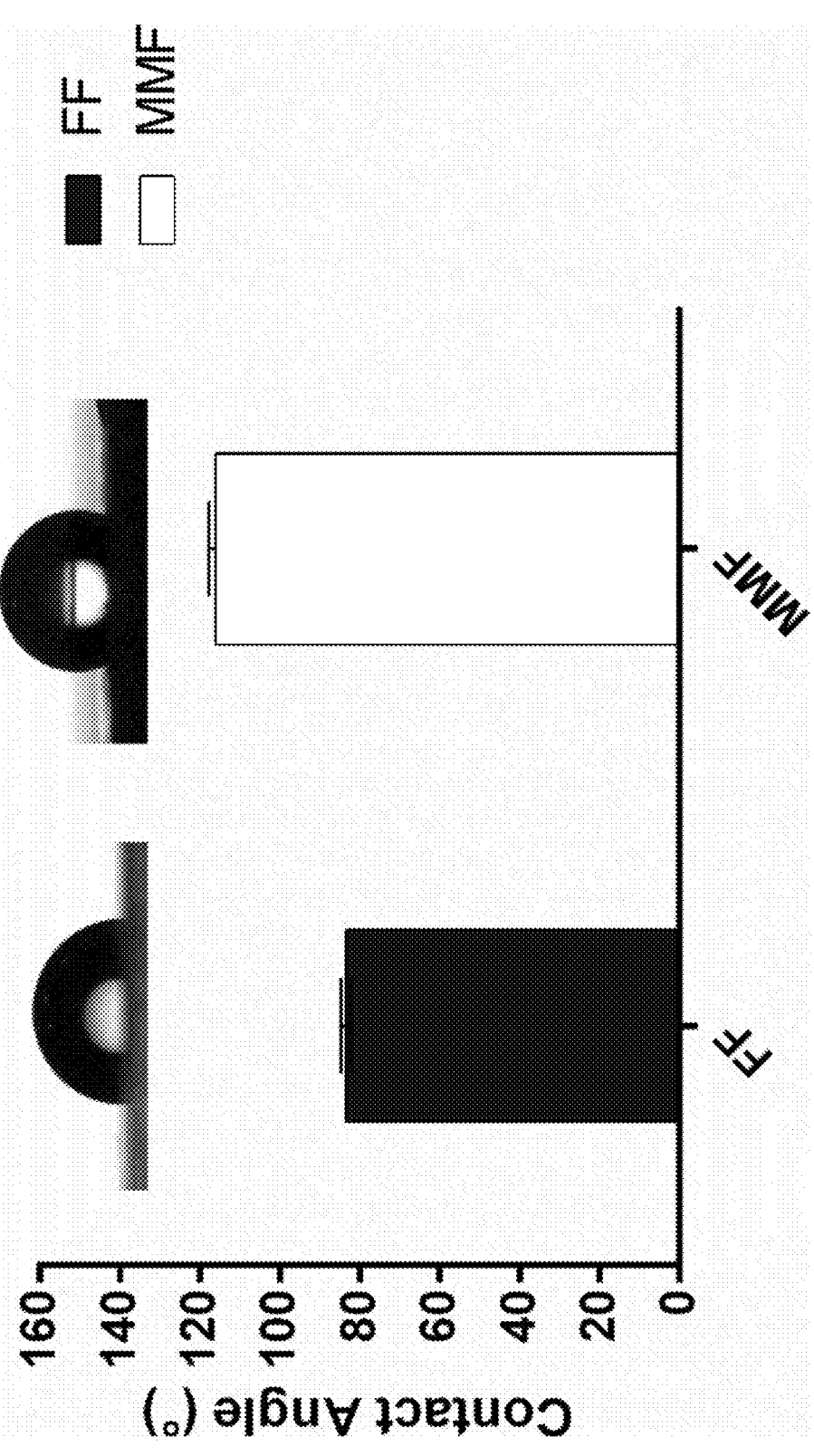
FIG. 5 is a bar graph showing water contact angles (WCA) of flat non-structured PLGA films (FF) and MMF determined with a droplet of DDW on the film at ambient temperature. Values are the mean±s.d. of three measurements. FF represents a control.

The surface wettability of the obtained FF and MMF samples was evaluated by water contact angle (WCA) measurement. The measurements were conducted with a droplet of double-distilled water (DDW) using an Easy Drop contact angle goniometer (FM40Mk2, Krüss GmbH, Hamburg, Germany) at room temperature and ambient humidity. (WCA of different exemplary samples are represented in FIGS. 5 and 8).

Counter Surface

The adhesion strength of the different FF and MMF samples was evaluated using a flat and smooth rigid glass as counter-surface (substrate). The flat glass was 26*76*1 mm (Paul Marienfeld GmbH & Co KG, Am Woellerspfad 4, Lauda-Koenigshofen, 97922 Germany) with an average roughness Ra about 30 nm and with a water wettability angle of about 76° measured using the same EasyDrop (FM40Mk2 KRUSS GmbH, Germany). As described hereinbelow, some adhesion experiments are conducted under wet contact conditions (DDW). For this reason, a PVS belt of 1 mm height was glued on the hard glass contour to retain the liquid.

Experimental Set Up (Adhesion Test)

Adhesion performance of the different samples was evaluated on a customized two-axis tribometer designed and built recently in the Department of Mechanical Engineering at Azrieli College of Engineering Jerusalem. This tribometer was specifically designed to evaluate tribological performances (such as friction and adhesion) of micro patterned and biomimetic soft elements upon contacting a substrate (counter face). These tests can be conducted under dry or wet contact conditions according to need.

Figure 6:
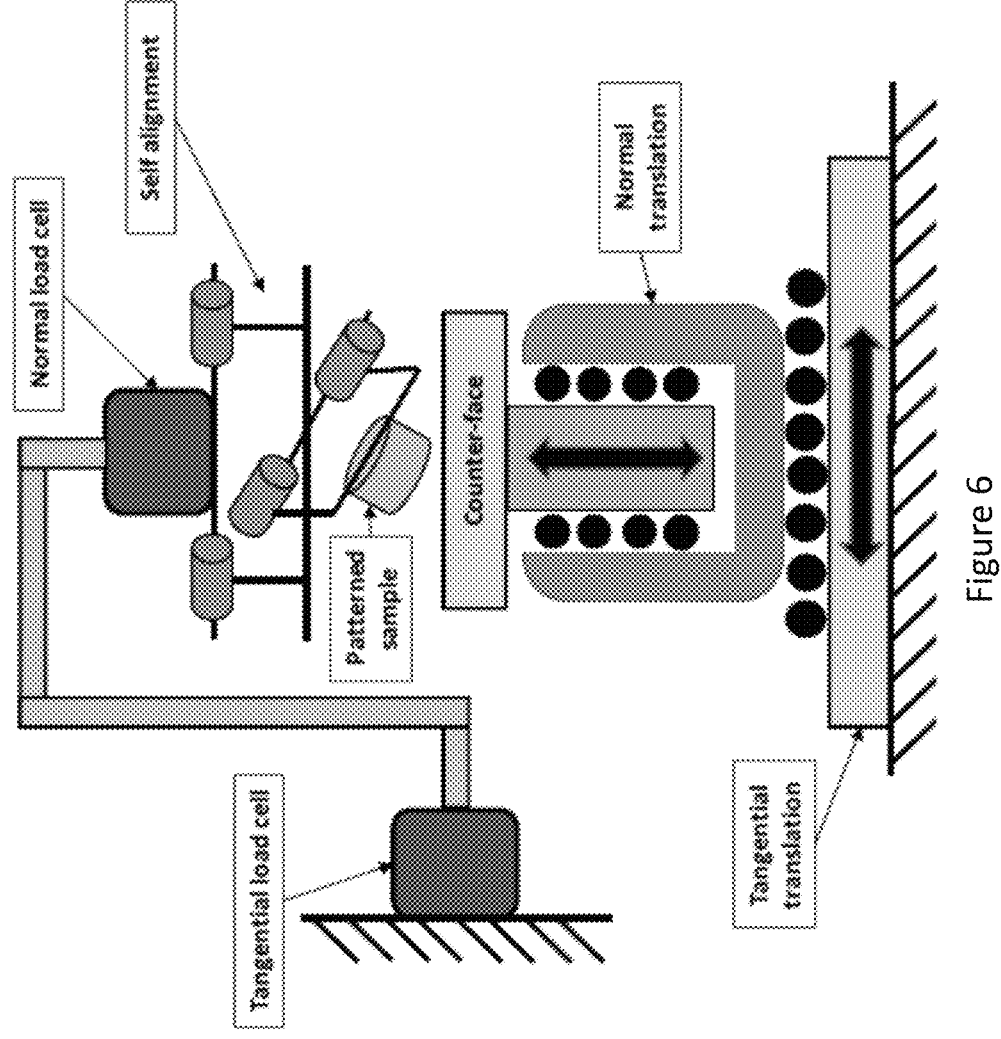
FIG. 6 shows a schematic representation of the customized tribometer, as used herein for measurements of the adhesion strength.

FIG. 6 illustrates a general schematic of the used tribometer that incorporates two main units used for driving and measuring purposes. The drive unit contains three translation stages amongst which two are motorized while the third is manual. These stages allow adjustment of the location of the contact and loading the system (apply normal and lateral displacements between the sample of micro-patterned surface and the counter-face "glass plate in the present study"). This is achieved by driving the counter-face sample in the three directions while the patterned sample is kept immobile. Movements in normal and lateral directions are motorized using X-LSM025A-E03 and X-LHM050A-E03 ZABER motors for normal and lateral displacements, respectively. However, adjusting the location of the patterned sample with regard to the counter-face sample in a third direction is achieved manually using a micrometric translation stage (ZABER model TSB28M-MH2). The measurement unit consists of two high resolution load cells (FUTEK's FSH00092-LSB200, resolution 0.1 mN) that register the in situ variation of normal and tangential forces generated in the contact during a test. The operating and control software was written in a LabVIEW environment. The measurements were sampled with a multifunctional data acquisition board Lab-PC-NI USB-6211 (National Instruments Co., Austin, Texas) and processed using LabVIEW software. In addition, to ensure full flat-on-flat contact between the mating surfaces (patterned sample and flat glass in the present study) and to fulfil the essential "equal load sharing" principle in tribology testing of patterned surfaces, the current study uses a passive self-aligning system based on the principle of two free rotation axes. The small metallic axes are assembled to allow rotation freedom degrees in the axes perpendicular to the normal direction (see illustration in FIG. 6).

Adhesion Test Experimental Procedure

Figure 7:
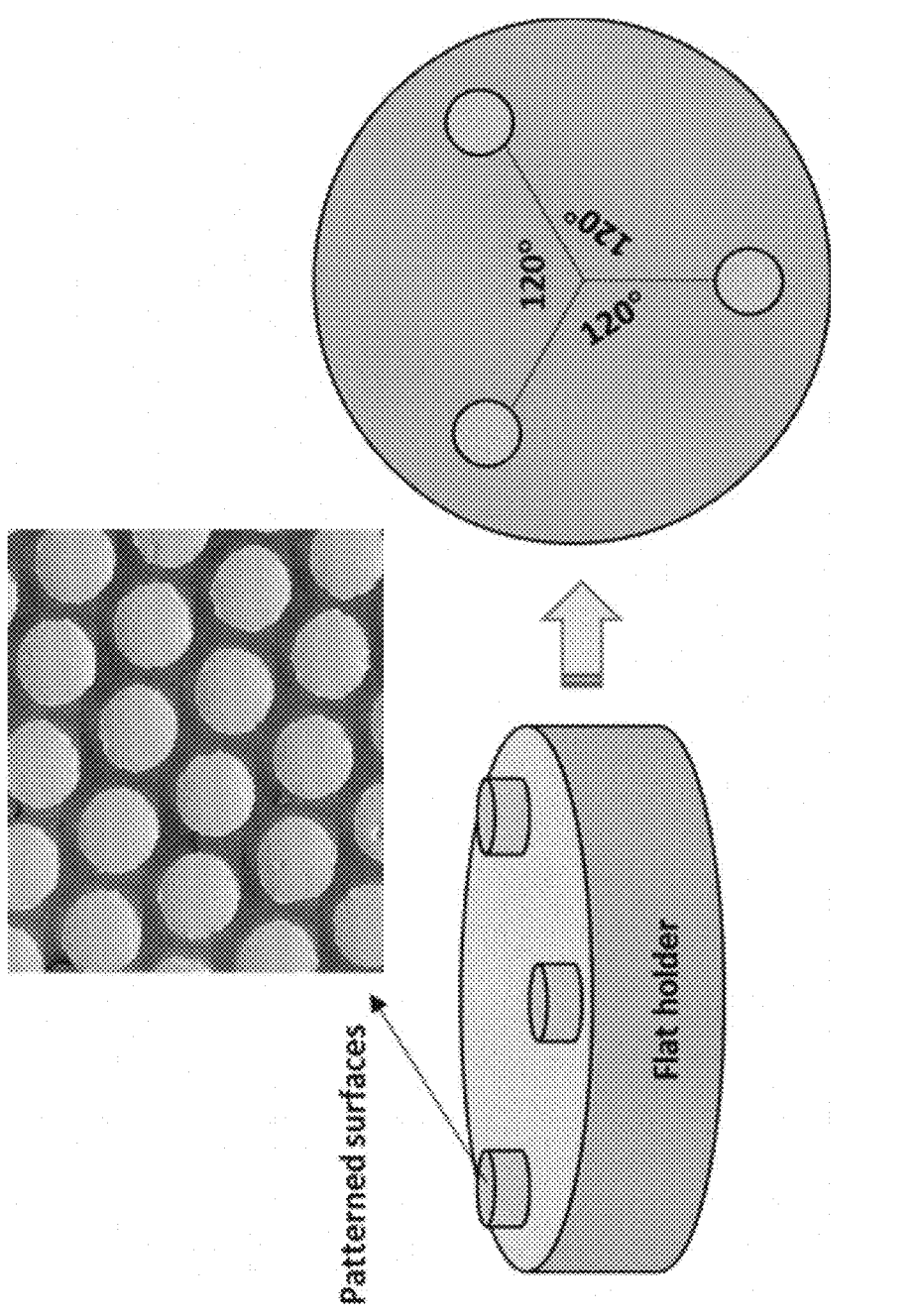
FIG. 7 shows a schematic representation of patterned sample assembly for the adhesion test.

As mentioned hereinabove, two PLGA samples were tested: (i) a control reference smooth sample (FF), and (ii) patterned mushrooms-shaped microstructure (MMF). For each test or repetition the patterned sample (or flat reference sample) consists of three small cylinders of 2 mm in diameter and 1 mm high that were punched out from the prepared PLGA film (FIG. 7). These small cylinders were then glued to a flat holder, itself mounted on the self-alinement system of the tribometer. The small cylinders were angularly separated with 120 degrees on the flat holder to guarantee symmetrical load repartition during adhesion tests. It is important to note that when gluing the cylinders onto the flat holder, a flat glass was used to flatten the surfaces of the different cylinders so that all are aligned in the same plane.

Once the samples are mounted, the measurement system and the self-alignment are calibrated by resetting the load cells to eliminate the effect of mass gravity. Calibration was performed after each sample replacement. Adhesion tests consist of bringing the patterned microstructure samples into contact with the glass counter-face at a constant loading speed of 0.3 mm/s until the predefined normal load is reached. Then a certain dwell time is spent while the system is being loaded and before the translation stage is withdrawn in the normal opposite direction at a constant velocity of 0.3 mm/s. The normal load cell measures and registers the variation of generated pull-off force. This study also investigates the influence of the normal preload through tests performed under normal preloads of 0.2, 0.5, and 1 N. Adhesion experiments were performed under dry and wet (distillated water) contact conditions. All experiments were performed at room temperature of 25 C°±1 C.° and under a relative humidity of 45%±5%.

Statistical Analysis

Statistical comparisons between the two groups were evaluated with Student's t-test (unpaired t-test, two-tailed) using GraphPad Prism, Version 6 (GraphPad Software, Inc., San Diego, CA). Differences were considered significant if $P<0.05$.

Figure 12:
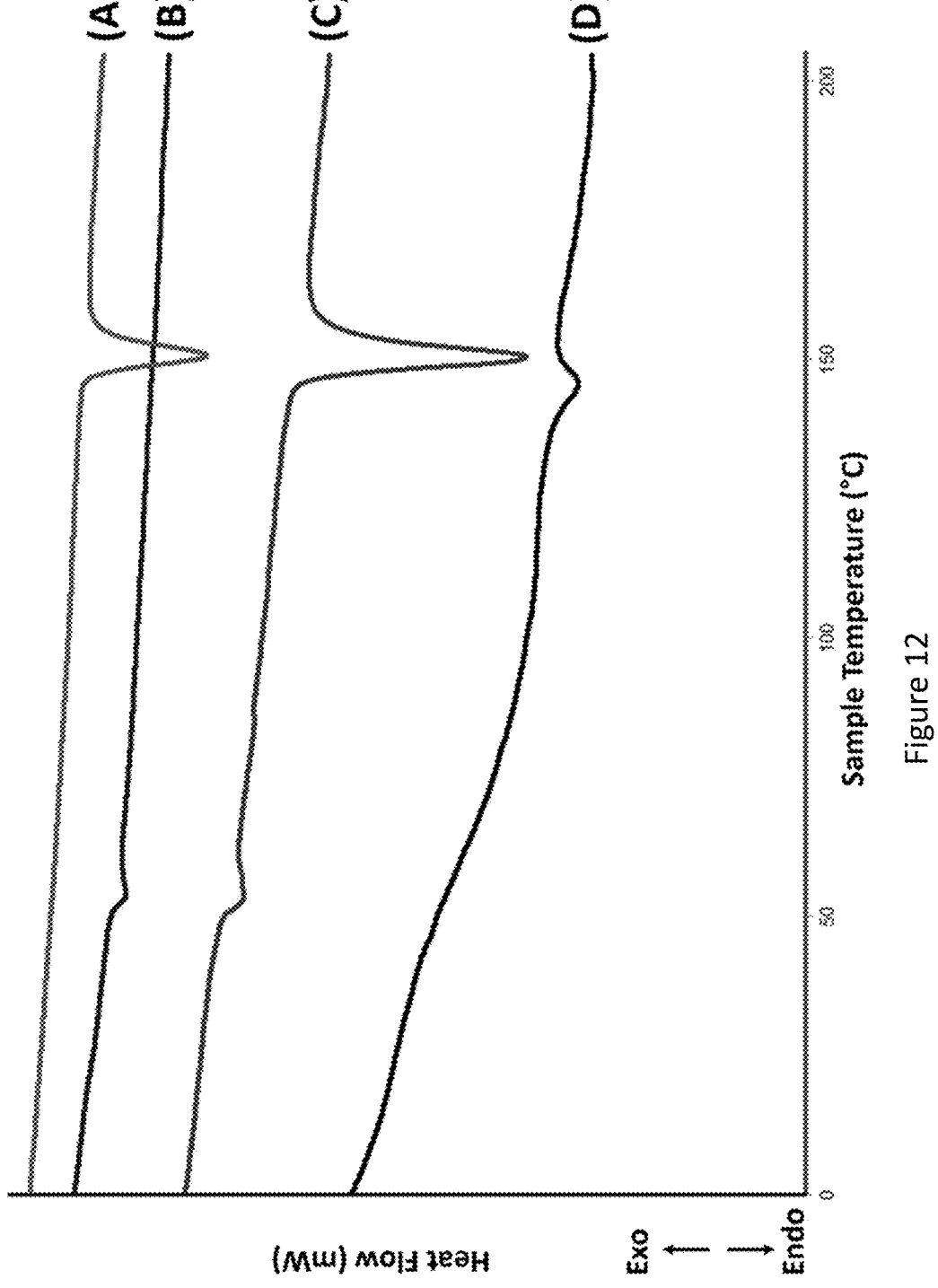
FIG. 12 is a graph showing differential scanning calorimetry (DSC) thermograms of (A) clotrimazole, (B) PLGA, (C) clotrimazole-loaded PLGA film (FF-CTZ50), and (D) clotrimazole-loaded PLGA film (FF-CTZ50).

Differential Scanning calorimetry (DSC) measurements of the obtained films loaded with CTZ has been performed (see FIG. 12). Additionally, the release profile of CTZ form the CTZ loaded films has been evaluated according to a conventional release protocol (see FIG. 13A-13D).

ATR-FTIR spectra were measured by a PerkinElmer Spectrum 100S spectrometer equipped with a universal ATR sampling accessory. The transmission spectra were recorded over 520-4000 cm−1, using 4 scans with a resolution of 4 cm−1.

In Vitro Drug Release Studies

Samples of FF-CTZ50 and MMF-CTZ50 (equivalent to 6 mg of the drug) were placed in 20 mL of simulated saliva containing 1% tween 80 (pH 6.8 and pH 5.5) and maintained at 37° C. in a rotary incubator (150 rpm). At predetermined time intervals, 1 mL samples were withdrawn from the release medium and CTZ concentrations were determined using a UV-Vis spectrophotometer at a wavelength of 261 nm. After each measurement, the samples used were returned into the original medium solution to maintain a constant volume of surrounding release medium (sink conditions were maintained during the entire dissolution experiment). The concentrations of CTZ calibration curves in simulated saliva containing 1% tween 80 (pH 6.8 and pH 5.5) ranged from 0 to 600 μg/mL.

In Vitro Mucoadhesion Studies

Mucoadhesive capacity of FF-CTZ50 and MMF-CTZ50 was evaluated by adapting the displacement method using an agar plate normalized with mucin. Briefly, separate agar and mucin solutions in PBS (pH 6.8 and pH 5.5) were prepared, following which the agar solution was left to cool down to 50° C. before adding the mucin solution with stirring. The mixture was then rapidly poured into plates of 8.5 cm in diameter and the plates were wrapped with parafilm to prevent evaporation of water from the media and left at room temperature for 1 h to set and transferred to 4° C. for storage. To standardize the media before using for dynamic adhesion measurements, the agar/mucin plate was equilibrated for 1 h to the test conditions of 37° C. Samples of FF-CTZ50 and MMF-CTZ50 were placed at the top of the agar/mucin plates. Then, a force of 1 N was applied to each sample for 1 min. All plates were re-wrapped with parafilm to prevent any change in the humidity or drying out of the adhesion medium environment for the duration of the experiment. The plates were inclined at an angle of 30° and the samples allowed sliding down the plate. Distance covered by the films over different time intervals was recoded (n=5). Furthermore, the maximal adhesion strength of FF-CTZ50 and MMF-CTZ50 samples was determined, as described in section 2.7., using agar/mucin as the mucosal substrate under both pH 6.8 and pH 5.5 to simulate pH conditions in the oral environment.

Example 1

Clotrimazole-Loaded PLGA

PLGA films have successfully loaded with different w/w ratios of Clotrimazole (a model active agent). In brief, a PLGA solution (as described hereinabove in Materials and Methods section) was mixed with solid Clotrimazole (CTZ), so as to obtain a homogenous mixture. Subsequently, the resulting mixture was casted into a PVS mold, as described herein hereinabove in Materials and Methods section, to obtain a PLGA film with patterned mushroom-type microstructures. PLGA films loaded with varying amounts of CTZ have been successfully prepared by the Inventors (see Table 1 below).

As represented by Table 1, CTZ encapsulation efficiency in FFs ranged from 90.2±2% for FF-CTZ50 to 94.9±3.2% for FF-CTZ10. A slight decrease was noted as the CTZ/PLGA ratio decreased. However, encapsulation efficiency in MMF s was in the range of 72.9±4.2% for MMF-CTZ50 to 96.7±2.1% for MMF-CTZ10, with more pronounced decline as the CTZ/PLGA ratio decreased. The drug loading content for FFs and MMFs was closer for CTZ10 and CTZ20, however it was higher in the case of FF-CTZ50 compared to MMF-CTZ50. Overall, high drug loading content was obtained, especially for CTZ50 films. The surface pH of the films was determined to predict the possibility of any adverse effects that might be evolved in vivo due to acidic or alkaline pH that irritate the buccal mucosa. The human oral cavity has a pH normal range of 5.5-7 (Patel et al., 2012), and the measured surface pH of PLGA films was in the range of 6.4-6.65 (Table 1) and 5.56-5.7 (data not shown) in pH 6.8 and pH 5.5, respectively. This indicates that no mucosal irritation is expected in the oral cavity upon film application.

Figure 8A:
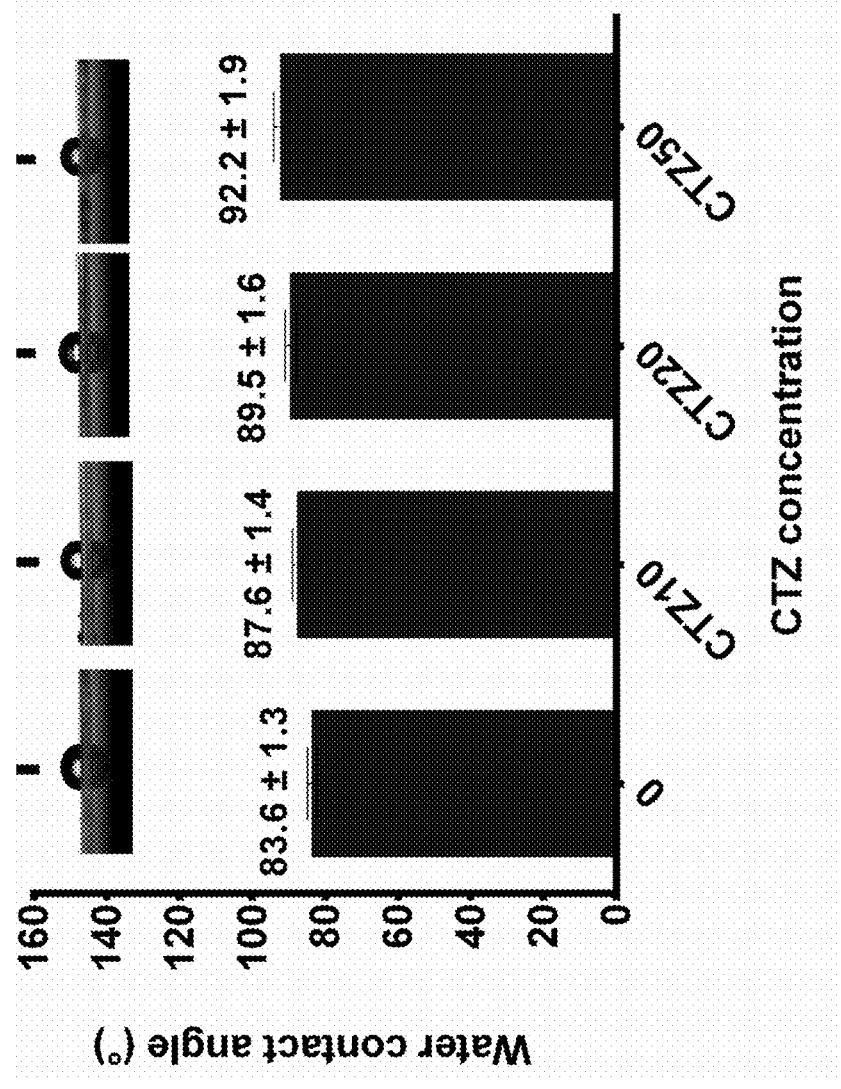
FIGS. 8A-8B are bar graphs showing water contact angle measurements for the obtained PLGA films. (8A) Representative images of contact angle measurements for PLGA FF with different clotrimazole (CTZ) concentrations. (8B) Representative images of contact angle measurements for PLGA patterned films (e.g. exemplary films of the invention) with different CTZ concentrations. Values are mean±standard deviation (n=3). MMF-CTZ10, MMF-CTZ20, MMF-CTZ50 are CTZ loaded MMF films prepared by casting an organic solution (e.g. chloroform solution) containing PLGA and CTZ, wherein a w/w concentration of CTZ within the organic solution is 10%, 20% and 50% respectively.
Figure 8B:
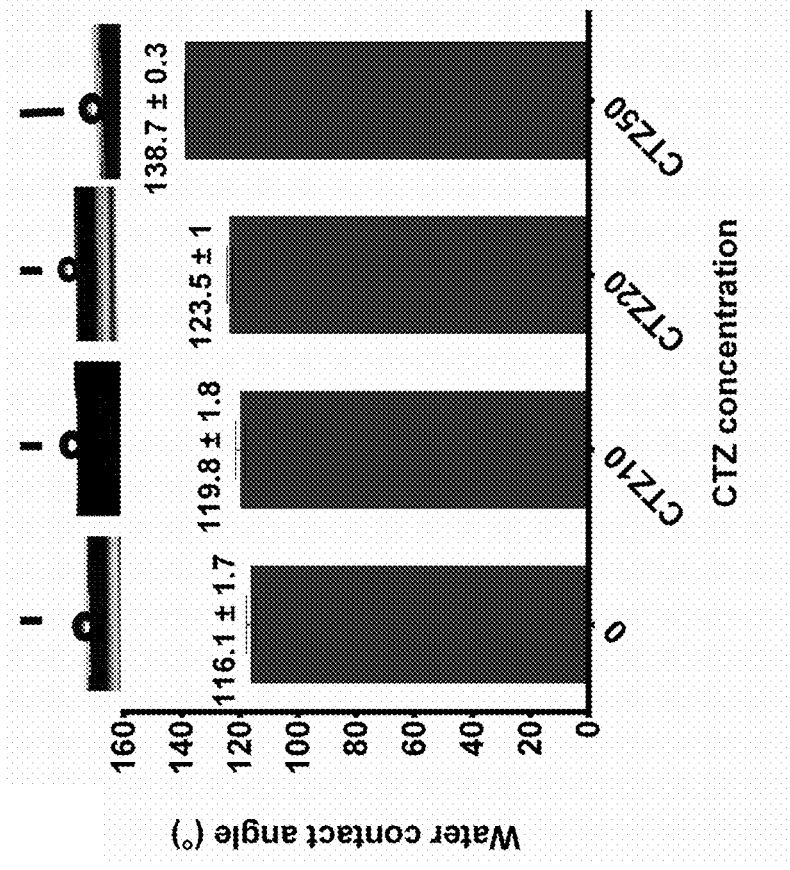

The wetting behaviour of a material depends on various factors such surface texture/roughness and surface chemistry. However, it is difficult to distinguish the effects of each factor due to the interplay and/or overlap of two or more factors in each system. Changing the surface geometry/roughness can be used to tune the contact angle. By increasing surface roughness the apparent contact angle increases for hydrophobic materials. Here, the effect of drug loading and surface texturing on the film wetting angle was evaluated, by measuring the water contact angles of different FF and MMF formulations (FIGS. 8A-B). The measured water contact angle of MMF formulations was larger compared to FF formulations (e.g. by about 35-40%).

The encapsulation of CTZ into the films enhanced their surface hydrophobicity compared to blank films. For example, contact angles of MMF CTZ 10, MMF CTZ 20 and MMF CTZ 50 were greater by about 4%, about 8%, and about 23%, respectively as compared to a similar MMF devoid of CTZ.

To simulate physiological pH of oral environment, the wettability of FF, MMF, FF-CTZ50 and MMF-CTZ50 was further evaluated by measuring the contact angle of a droplet of PBS (pH 6.8 and pH 5.5) and the results were in agreement with those obtained using water (data not shown). These findings indicate that the hydrophobic properties of PLGA surfaces can be altered not only by chemical modification, but also by surface texturing.

Figure 11A:
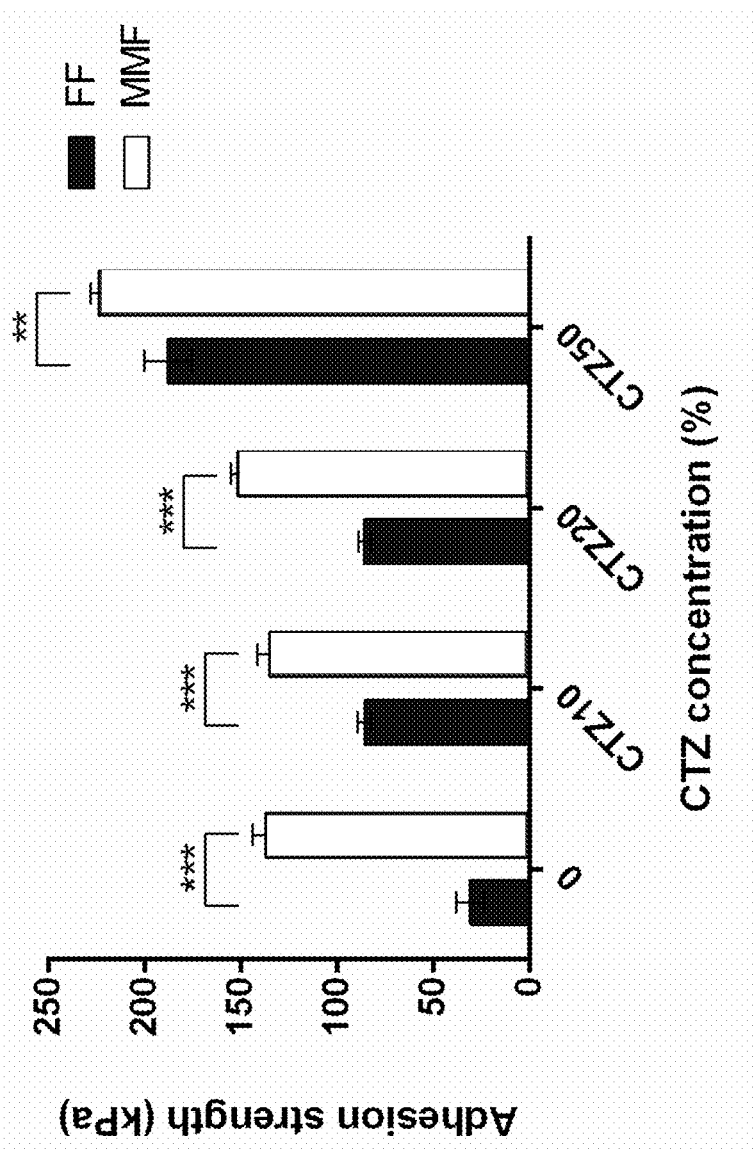
FIGS. 11A-11B are bar graphs showing maximal adhesion strength of FF and MMF samples (e.g. exemplary films of the invention) tested at 1 N normal preload under dry (11A) and wet (11B) conditions (PBS, pH of 6.8). Values are the mean±s.d. of three experiments; P<0.01, *P<0.001. FF represents a control.

In adhesion tests the normal load decreases during the displacement of the translation stage in the normal opposite direction. An adhesion force resists the separation of the mating surface and, therefore, appears negative in the graph. The maximum adhesion force is recorded for each test or repetition at the separation point (complete detachment). The adhesion strength, i.e. average value of the maximum adhesion force obtained from three repetitions and normalized by the nominal contact surface, as well as the relative standard deviation, were computed for each sample. FIG. 11A presents the adhesion strength and standard deviation as a function of CTZ concentration for tests conducted in dry contact under 1 N normal preload. It can be seen that, compared to FF, MMF samples generate more adhesion (adhesion strength of the MMF was about 140 KPa, whereas FF samples exhibited an adhesion strength of only about 40 KPa, e.g. about 2.5 fold increase of the adhesive strength). This increases with increasing CTZ concentration in both FF and MMF samples (e.g. MMF CTZ 50 sample exhibited an adhesion strength of about 220 KPa, which is about 1.6 times greater than a similar MMF sample without CTZ).

Figure 11B:
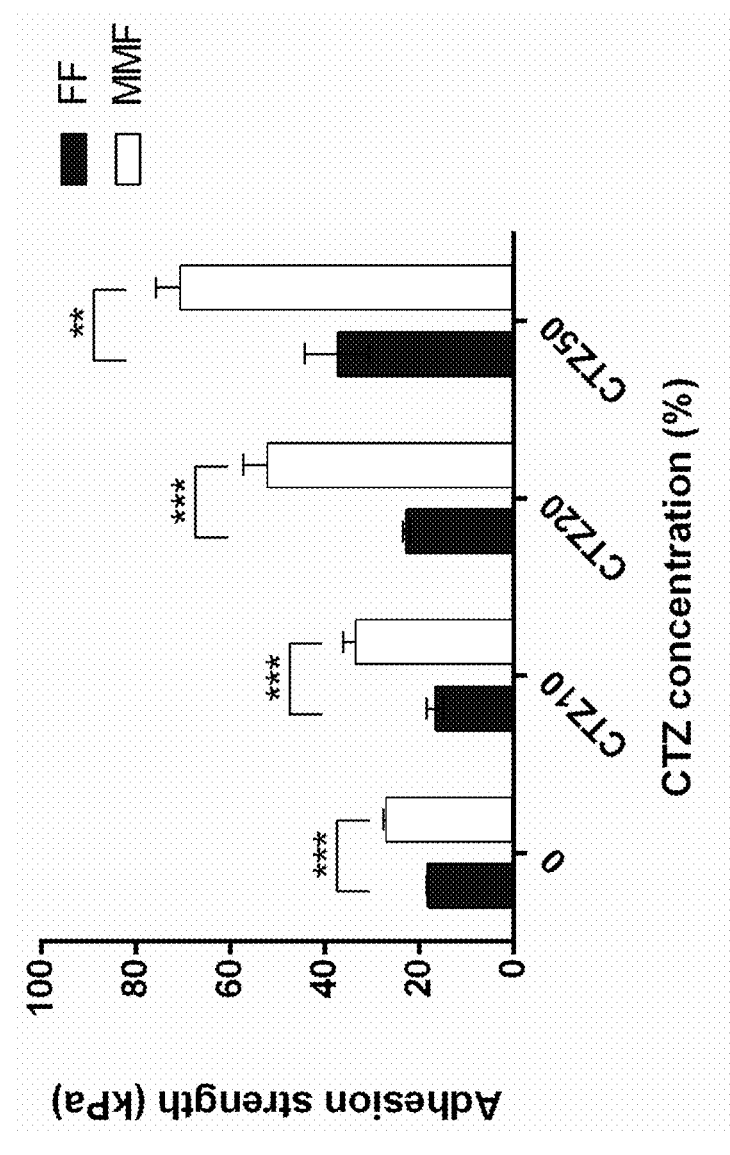

FIG. 11B presents the adhesion strength and relative standard deviation as a function of CTZ concentration for tests conducted under wet conditions (PBS-pH 6.8) using 1 N normal preload. Compared to dry contact, under wet condition MMF samples generate much higher adhesion strength (at least twice as high) compared to FF sample tested under the same conditions. For example, MMF CTZ 10, MMF CTZ 20 and MMF CTZ 50 exhibited an adhesion strength (under wet conditions) of about 30, about, 50, and about 70 KPa, respectively, whereas a similar MMF sample without CTZ exhibited adhesion strength of about 25 KPa. The results represented in FIG. 11B confirm almost 3-fold increase in the adhesion strength of MMF samples loaded with CTZ as compared to compared to MMF sample without CTZ.

The increase in adhesion force of MMF sample loaded with CTZ compared to FF sample and MMF blank sample (without CTZ) under wet conditions can be explained by eventual capillarity forces that are expected to increase with increasing surface roughness. An additional contribution can be attributed to the elastic—plastic behaviour of the con-tacting summits, as well as the effect of possible adsorbed CTZ layer presented on the surface. Recalling that the only difference between FF and MMF samples is surface pattern-ing, these results tend to highlight that surface texturing, particularly based on biomimetic models, can be an appro-priate chose to improve adhesion capacity of polymers such as PLGA. Based on these findings, MMF-CTZ50 was selected for further investigation to guarantee high adhesive performance.

The surface morphology of the obtained films loaded with CTZ has been examined by HR-SEM, as described herein-above. Representative HR-SEM images are represented in FIG. 9.

Furthermore, WCA and adhesion strength (under dry and wet conditions) of the obtained films loaded with CTZ have been evaluated. The experimental results are summarized in FIGS. 8A-8B. It should be noted that the adhesion strength of the evaluated films was superior under wet conditions, compared to the adhesion strength under dry conditions (FIGS. 11A and 11B).

Figure 13A:
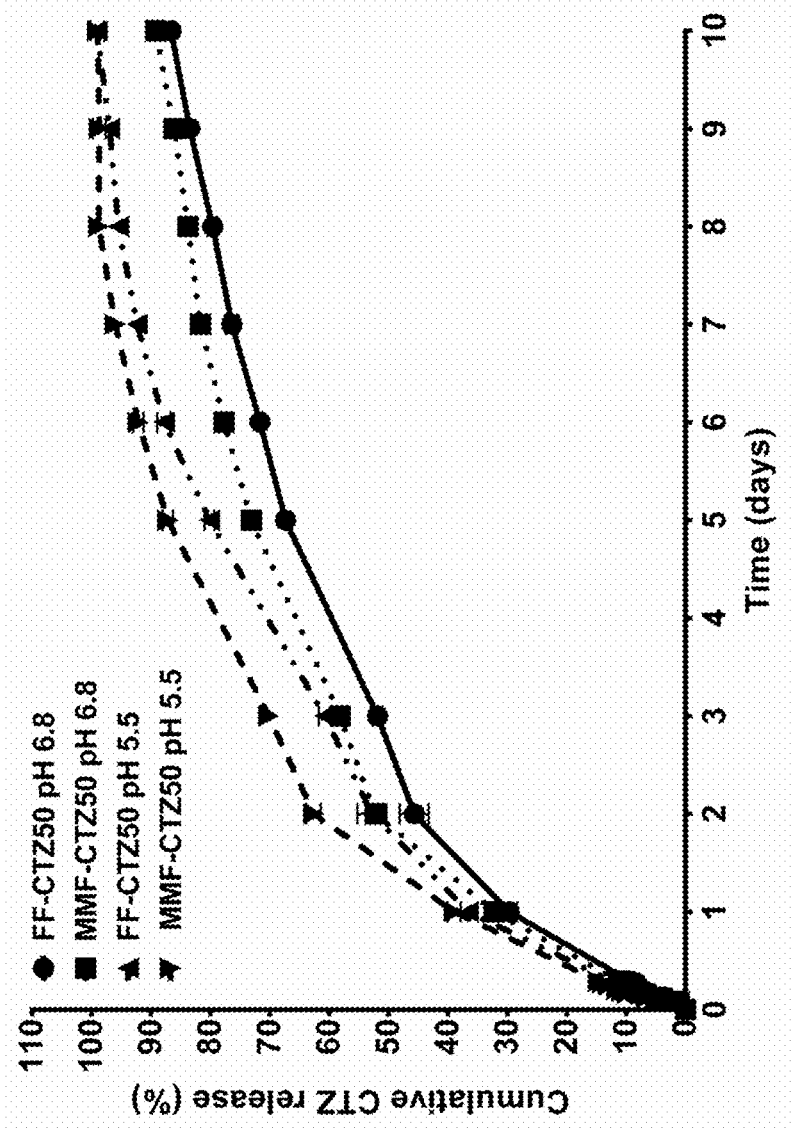
FIGS. 13A-D: 13A is a graph showing in vitro release of CTZ from FF-CTZ50 and MMF-CTZ50 (e.g., exemplary films of the invention) in simulated saliva containing 1% Tween 80 (pH 6.8 and pH 5.5, 37° C.) at different time intervals. Values are the mean±s.d. of four experiments.

Thermal analysis using DSC was performed for PLGA, CTZ, clotrimazole-PLGA (1:1) physical mixture, and CTZ-loaded PLGA film (FF-CTZ50). The first heating run at a heating rate of 10° C./min is shown in FIG. 6. DSC thermogram of the CTZ sample presents a characteristic endothermic peak at 145° C., and the thermogram of PLGA sample shows a glass transition temperature (Tg) at 50° C. The melting point present in the CTZ sample has shifted by 6° C. down to 139° C., which indicates a decrease of drug crystallinity.

films. As ATR irradiation penetrates samples to a depth of 2-15 μm, this indicates that the majority of the drug resides within the bulk of the film rather than at the surface. Additionally, ATR-FTIR spectra were measured for each film at three different positions to assess the homogeneity of the films. The spectra showed no significant difference indicating that the chemical and morphological composition of the films was uniform throughout (results not shown). To evaluate the potential application of CTZ-loaded films for local oral delivery, the in vitro release of CTZ from FF-CTZ50 and MMF-CTZ50 was tested in simulated saliva containing 1% tween 80 (pH 6.8 and pH 5.5) at 37° C. The simulated saliva was chosen to mimic the conditions in the oral cavity, and Tween 80 was used to enhance the solubility of CTZ in the release medium. CTZ release from both FF and MMF exhibited an initial burst release, accompanied by a sustained release phase, and the release was higher at lower pH (FIG. 13A). Additionally, CTZ release from FF was slightly slower than MMF. Diffusion of an appreciable of CTZ from the film surface layer, that could be weakly bound or adsorbed, most likely contributed to the initial burst release. To study the mucoadhesive properties of the obtained films, agar/mucin plate was used as a representa-tive mucosal substrate. In spite of the difference between porcine gastric mucin and native mucins, it is frequently used to evaluate mucoadhesive interactions due to reduced batch-to-batch variability and better reproducibility of results. First, the mucoadhesion of FF-CTZ50 and MMF-CTZ50 was assessed using an inclined agar/mucin plate method, in which the mucoadhesion is inversely related to the displacement of the film. Although the displacement of both FF-CTZ50 and MMF-CTZ50 was increased with time, regardless of pH, there were statistically significant differ-ences between them along the experiment duration (FIGS. 13B-C), indicating superior mucoadhesion potential of MMF-CTZ50. Second, in order to further assess the ability of films to adhere to mucosal surfaces, the maximal adhesion strength required for detaching the films from the surface of the agar/mucin was determined. The results revealed that the adhesion strength of MMF-CTZ50 is significantly high compared to FF-CTZ50 under both pH 6.8 and pH 5.5 (FIG. 13D).

Figures 13B, 13C:
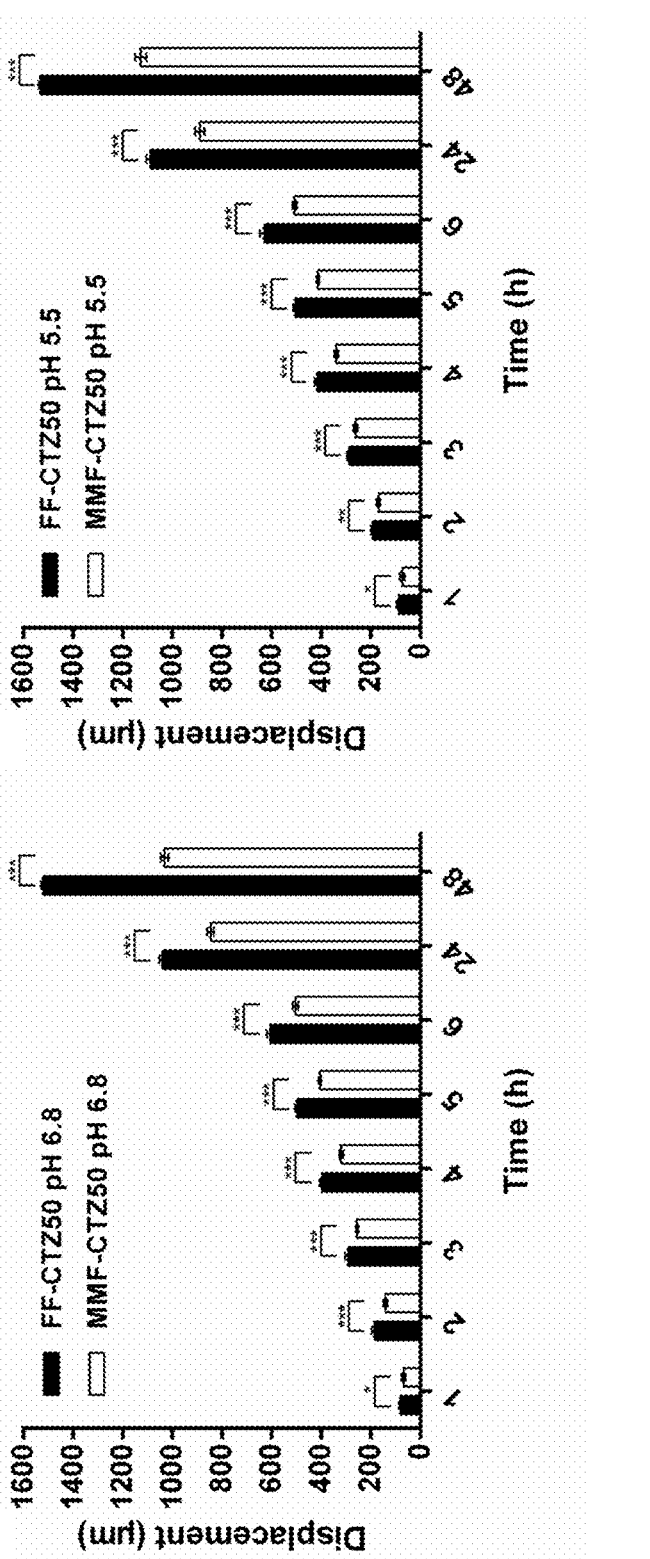
Figure 13D:
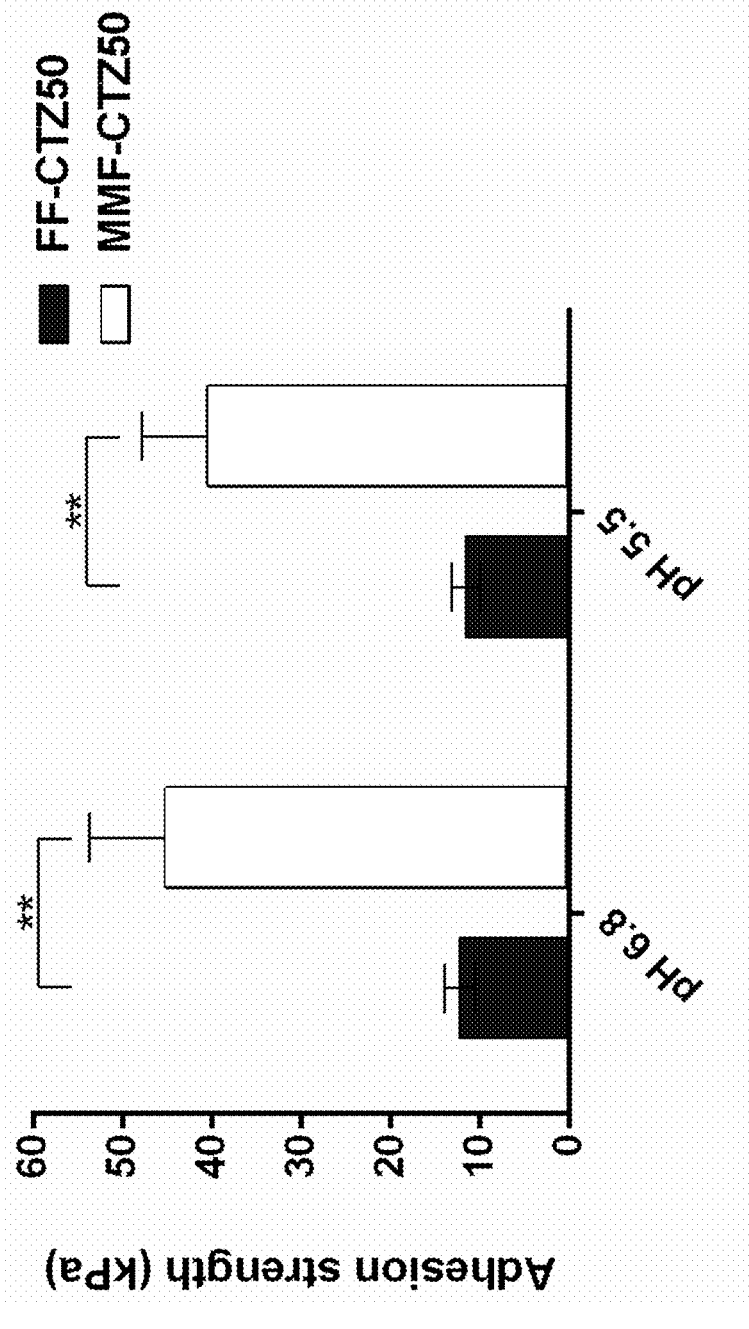

These findings are in agreement with the in vitro mucoad-hesion determined by the displacement method (FIGS. 13B-C). Apart from the above mentioned explanation, another

TABLE 1

Composition, encapsulation efficiency, drug loading content and surface pH of the obtained films (n = 3, mean ± s.d.).

| Formulation | CTZ (mg) | PLGA (mg) | Encapsulation efficiency (%) a | Drug loading content (%)[b] | Surface pH |
|---|---|---|---|---|---|
| FF | — | 25 | — | — | 6.63 ± 0.03 |
| FF-CTZ10 | 2.5 | 25 | 94.9 ± 3.2 | 8.67 ± 0.27 | 6.58 ± 0.02 |
| FF-CTZ20 | 5 | 25 | 93.6 ± 6 | 15.76 ± 0.86 | 6.44 ± 0.03 |
| FF-CTZ50 | 25 | 25 | 90.2 ± 2 | 47.41 ± 0.55 | 6.41 ± 0.05 |
| MMF | — | 25 | — | — | 6.65 ± 0.02 |
| MMF-CTZ10 | 2.5 | 25 | 96.7 ± 2.1 | 8.81 ± 0.18 | 6.49 ± 0.01 |
| MMF-CTZ20 | 5 | 25 | 83.7 ± 2.1 | 14.34 ± 0.31 | 6.40 ± 0.05 |
| MMF-CTZ50 | 25 | 25 | 72.9 ± 4.2 | 42.14 ± 1.42 | 6.40 ± 0.01 | a Encapsulation efficiency (%) = (amount of drug in film/amount of drug fed initially) × 100.
[b]Drug loading content (%) = [amount of drug/(amount of drug + amount of polymer)] × 100.

Figure 10:
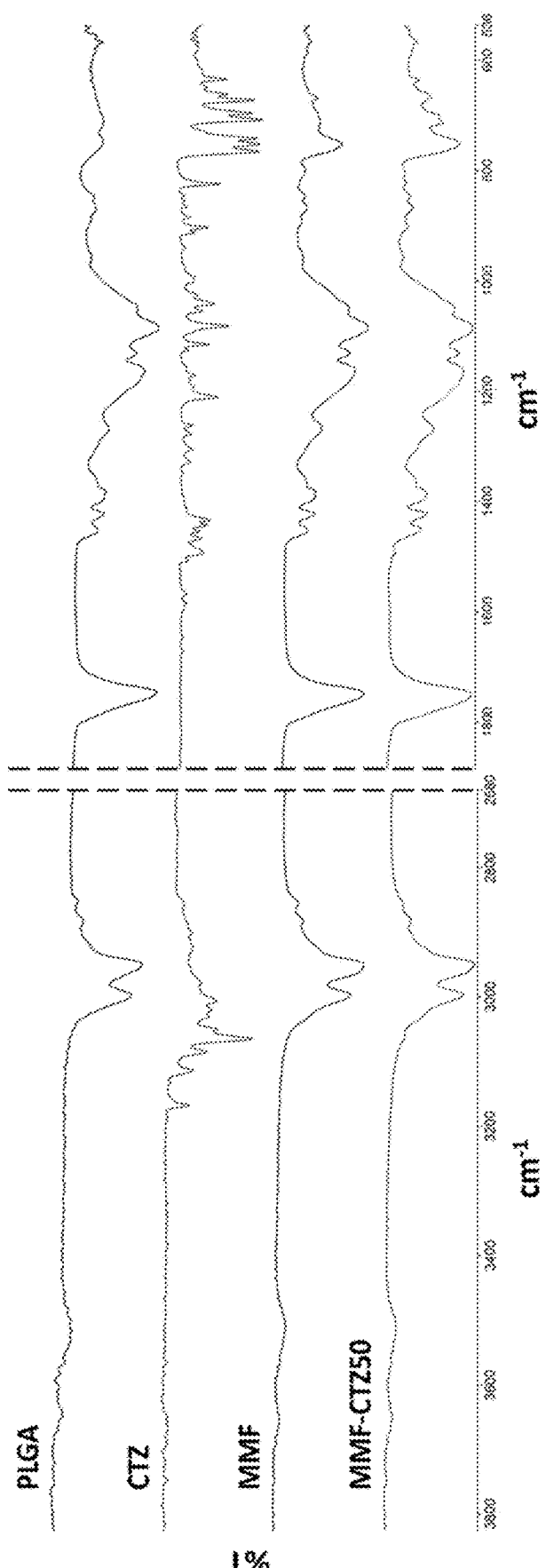
FIG. 10 is a graph showing FTIR (Fourier-transform infrared spectroscopy) spectra of PLGA, CTZ, MMF and MMF-CTZ50

ATR-FTIR spectra of CTZ, PLGA, MMF and MMF-CTZ50 were measured (FIG. 10). Despite the high drug loading content, CTZ was less evident at the surface of the possible explanation for the different performance of FF-CTZ50 and MMF-CTZ50 can be attributed to the enhanced conformal contact between the agar/mucin and PLGA textured surface. As the agar/mucin substrate is very compliant it can conform to the area between the PLGA microstructures with low elastic strain energy and without extensively deforming them. This enhanced interfacial contact area may lead to increased adhesion.

To this end, the inventors demonstrated herein a drug-loaded PLGA adhesive films based on biomimetic microstructures with great potential to improve adhesion under wet conditions, simulating the oral cavity environment and allowing for controlled drug release without adding other adhesive excipients. The obtained textured films loaded with CTZ were successfully fabricated and exhibited high drug encapsulation efficiency and loading content. Furthermore, the films of the invention loaded with an exemplary drug (CTZ) exhibited greater adhesion strength compared to non-drug loaded films, and compared to control non-patterned films. The films of the invention loaded with an exemplary drug (CTZ) substantially retained at the adhesion site for a time period of up to 48 h (see FIGS. 13B-C).

Example 2

Microstuctured PLGA Films

FIGS. 4A-B show representative top and side views of the morphology for the obtained PLGA mushroom microstructures. The shape and topography of the initial PDMS mushroom-shaped was fairly successfully replicated with PLGA with an intact cup diameter of 40 μm. These very encouraging results prove that the two-step molding technique can be successfully applied to replicate sophisticated microstructures shaped, even with non-conventional material in the field such as PLGA.

To evaluate the effect of surface texturing of PLGA films on the water contact angles, the water contact angles of FF and MMF were measured are presented in FIG. 5, in terms of mean values and standard deviations obtained from three different measurements performed using three different samples extracted from each PLGA film. The measured contact angle of MMF samples was larger compared to FF samples (116.1±1.7° and 83.6±1.3°, respectively), confirming that the hydrophobic properties of PLGA surfaces can be enhanced by surface geometry without any chemical treatment. These observations reveal that even though there is no significant difference between fibers and films, by means of surface chemistry, the hydrophobic properties of the tested surfaces can be enhanced by roughness without complex chemical treatment. A possible explanation for the increased contact angle of MMF samples is that different contact states form liquid-polymer drops and spontaneously adopt a so-called Cassie—Baxter state, in which the contact area of solid-liquid is a composite surface consisting of solid-liquid surface and gas-liquid surface resulting from trapped air pockets.

Figure 14:
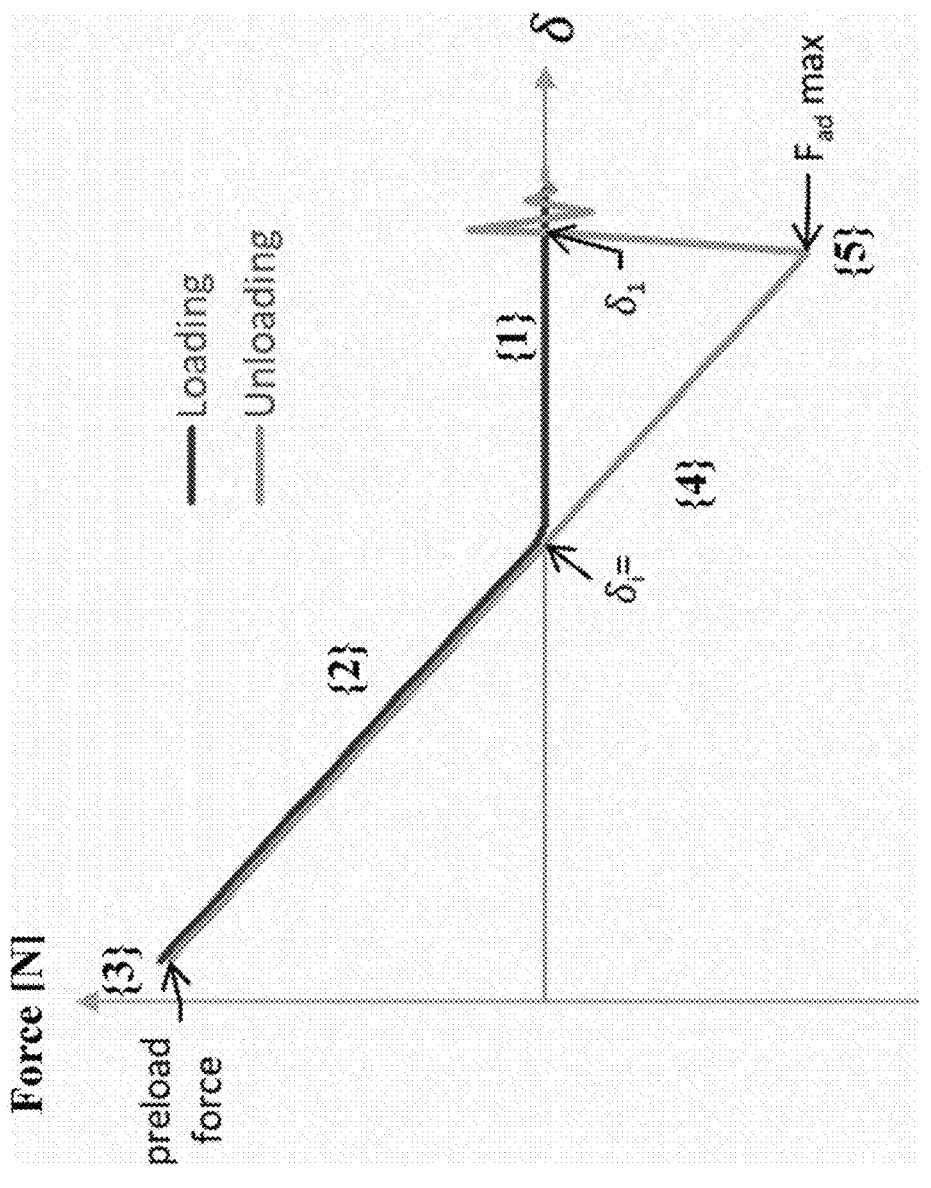
FIG. 14 is a graph showing the different steps of an exemplary adhesion test curve until the detachment point.

FIG. 14 exhibits a typical behavior of normal force variation during an adhesion (pull-off) test. This behavior can be divided into 5 representative stages: {1} The glass counter face approaches the patterned surface, reducing the initial gap between them, given that no contact occurs during this stage, thus the normal load remains null. Stage {2} consists of loading the system once a first contact is obtained until the desired predefined normal load is reached. The system can be maintained in the same position for a given dwell time {3}. Then, {4} the glass counter face is moved in the opposite normal direction leading to reduction of the applied normal load that will appear negative in the graph if the tested patterned surfaces are adhesive. The maximal negative value of the normal load reached at the separation point {5} is systematically recorded and considered as the maximal adhesion force for a given test. Each sample configuration was repeated three times, and the average value of the maximum adhesion force as well as the standard deviation were calculated and presented in FIGS. 15A-15B.

Figure 15A:
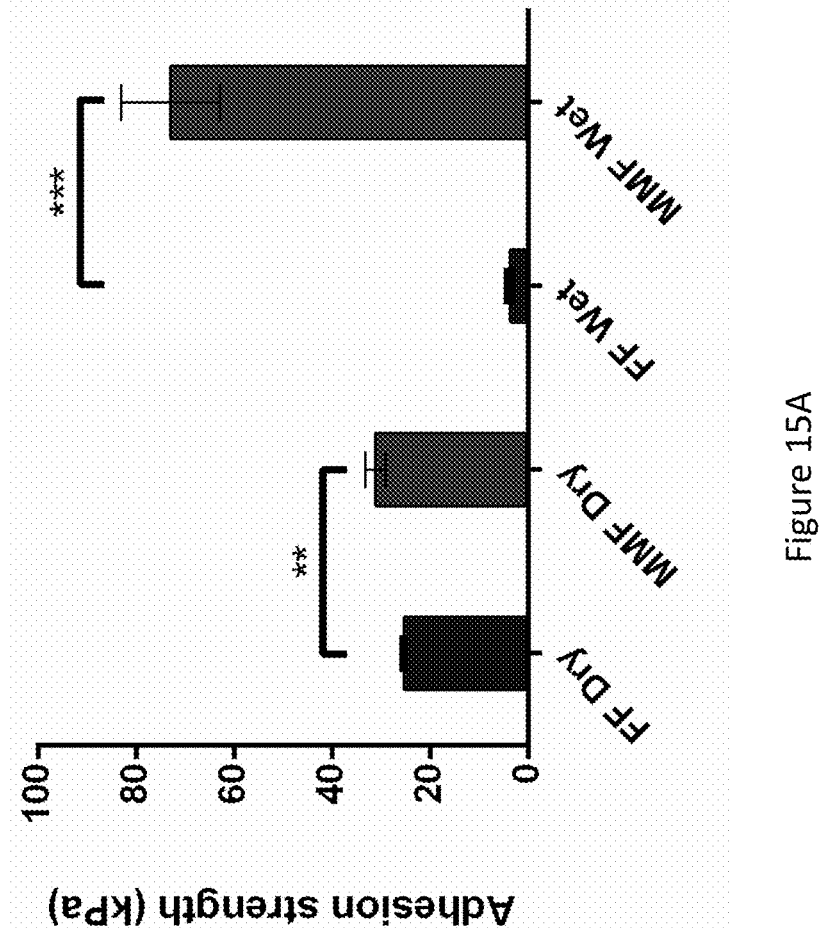
FIGS. 15A-15B are bar graphs showing maximal adhesion strength of FF and MMF samples (e.g. exemplary films of the invention) tested at 0.2 N (15A) and at 1N (15B) normal preload under dry and wet conditions. Values are the mean±s.d. of three experiments; P<0.01, *P<0.001. FF represents a control.

As noted above, adhesion experiments of FF and MMF samples were conducted under dry (air) and wet (DDW) contact conditions and different preloads of 0.2, 0.5 and 1 N. After each test or repetition an adhesion strength (in kPa) was calculated by dividing the recorded maximum adhesion force by the nominal contact area of the sample. FIG. 15A shows the mean value of the maximal adhesion strength and standard deviation obtained from three different repetitions for both FF and MMF samples tested under dry and wet conditions at the lowest normal preload (0.2 N). Regardless of contact environment condition, MMF sample generates significantly higher adhesion strength compared to FF sample. The difference between the 14 samples in term of adhesion strength becomes more pronounced under wet condition. Adhesion strength of FF sample is reduced when tested under wet condition compared to dry condition, whereas the adhesion strength of MMF sample is increased under wet condition.

Figure 15B:
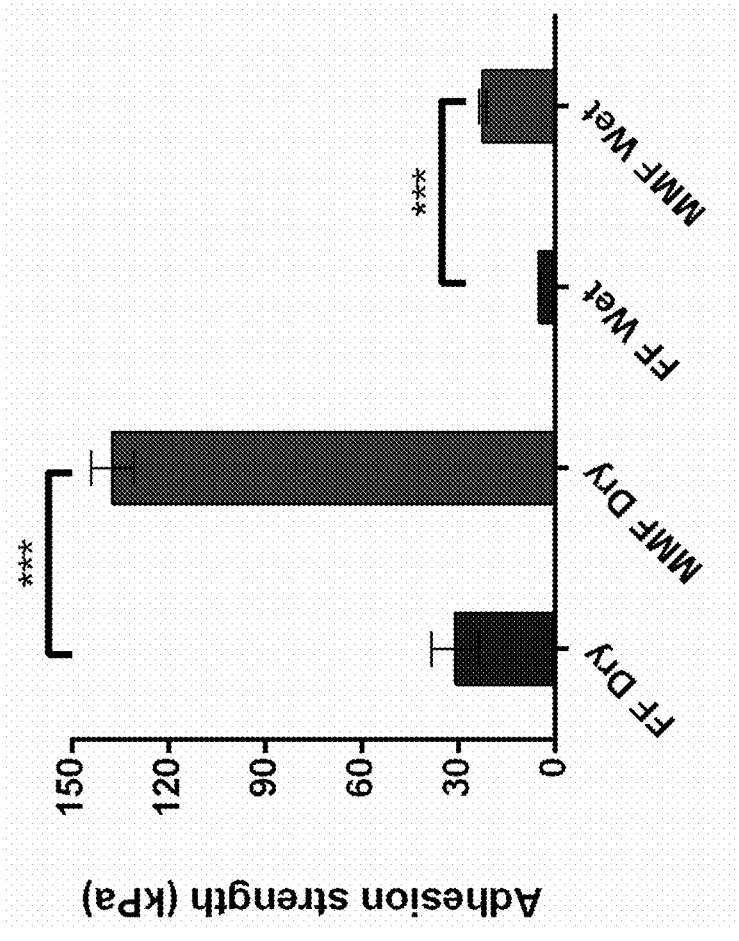

FIG. 15B presents the average value of the maximal adhesion strength and standard deviation obtained from three different repetitions for both FF and MMF samples tested under dry and wet conditions, when the highest normal preload (1 N) was applied. In results obtained under the minimal normal preload, regardless of contact conditions, the MMF sample still generates significantly higher adhesion strength compared to FF sample. However, under the high normal preload, both FF and MMF samples generate higher adhesion strength under dry contact.

Several additional points arise from FIGS. 15A-15B. These results prove that surface texturing based on a biomimetic concept can improve the adhesion strength of PLGA, which is a polyester that is typically non-adhesive without adding any additional excipients. Moreover, while the water contact angle of MMF sample (see FIG. 5) is greater compared to FF sample, MMF sample exhibits higher adhesion strength. Without being limited to any particular theory, it is postulated that the high adhesion of microstructures is most likely due to a contact subdivision effect, which is well-known in the art.

Figures 16A, 16B:
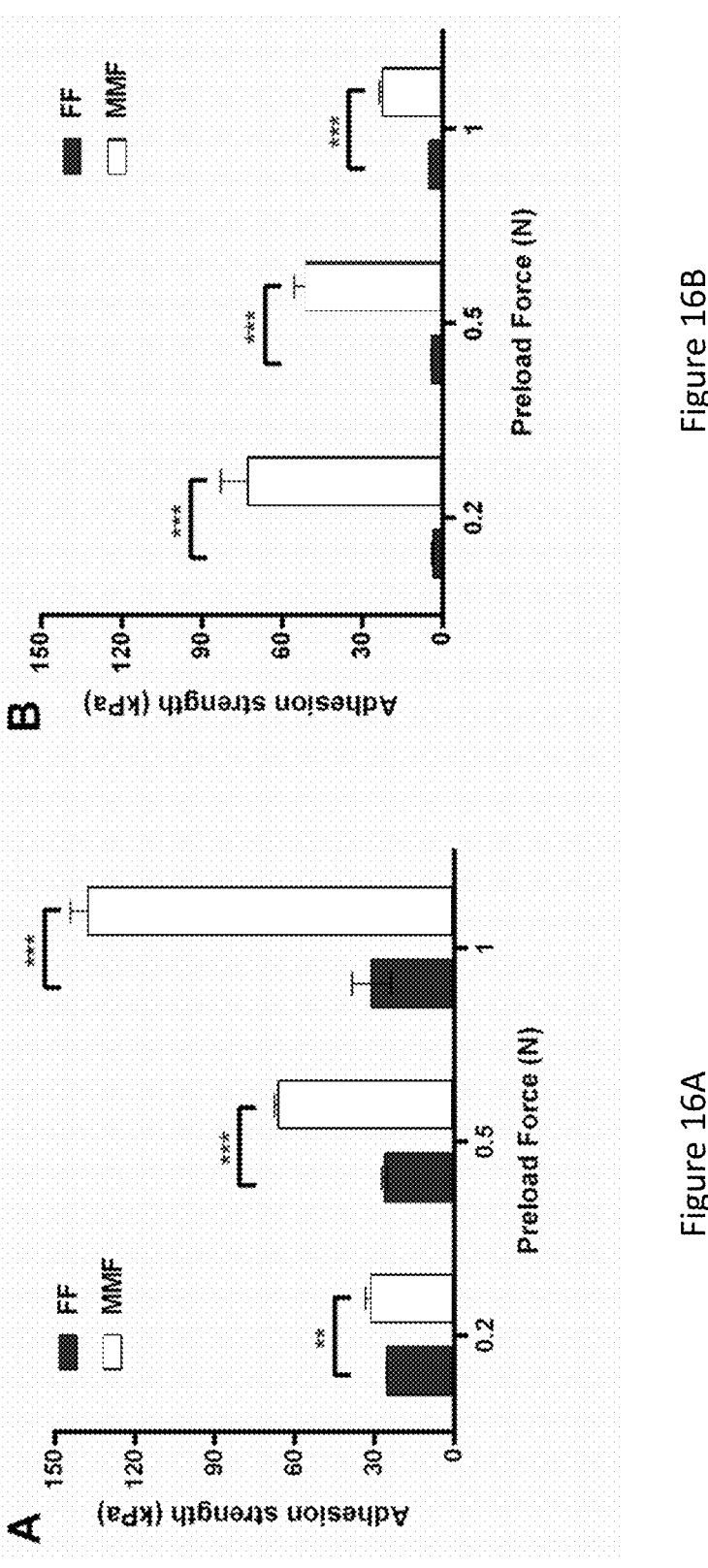
FIGS. 16A-16B are bar graphs showing Maximal adhesion strength (in KPa) of FF and MMF samples (e.g., exemplary films of the invention) tested at different normal preloads under dry (A) and wet (B) conditions. Values are the mean±s.d. of three experiments; P<0.01, *P<0.001. FF represents a control.
Figure 17:
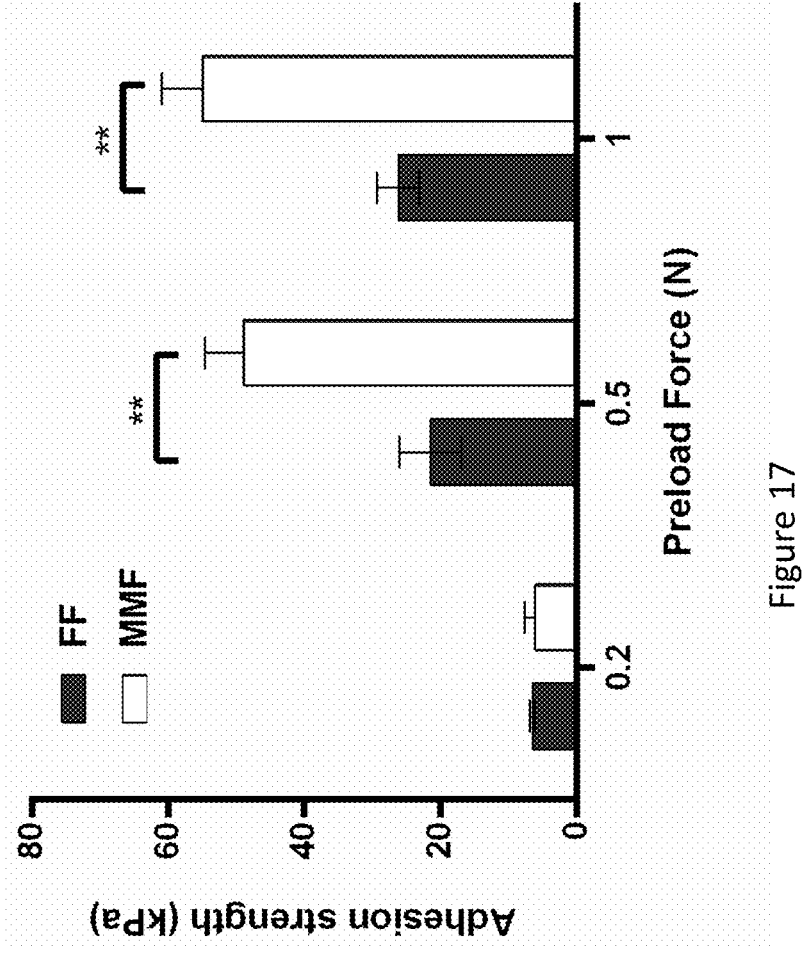
FIG. 17 is a bar graph showing maximal adhesion strength (in kPa) of FF and MMF samples (e.g. exemplary films of the invention) tested at different normal preloads on agar substrate. Values are the mean±s.d. of three experiments; **P<0.01. FF represents a control.

FIGS. 16A and 16B show the results of the two samples described hereinabove, tested under different normal preloads. The FF sample generates more or less constant adhesion strength under the different applied normal preloads whether under dry or wet conditions. Without being limited to any particular theory, it is postulated that the adhesive performances of MMF sample, made of PLGA, may be influenced by both the applied normal preload and contact environment conditions. The adhesive strength of MMF sample increases with increasing normal preload under dry contact condition, whereas it decreases with increasing normal preload under wet condition.

Without being limited to any particular theory, it is postulated that under dry condition, adhesion results mainly from van der Waals interactions and capillary forces; adhesion is magnified in the MMF samples due to a contact subdivision effect. However, under wet condition, van der Waals forces cannot explain higher adhesion under wet conditions. Under wet condition the adhesion strength of MMF is distinctly high compared to FF samples (20-fold at 0.2 N, 12-fold at 0.5 N and 5-fold at 1 N). Without being limited to any particular theory, it is postulated that such an improvement of the adhesion strength is due to the possible contribution of air bubbles entrapped between the mushroom-shaped microstructures and the glass counter-face. The entrapped air volume may expand during pull-off, leading to a pressure reduction and thus to a suction effect causing increased adhesion strength. This effect of air bubbles may be influenced by the applied normal preload, and consequently inducing a reduction in adhesion with increasing normal preload as obtained from the present study (FIG. 16B). Without being limited to any particular theory, it is postulated that the opposite tendency between dry and wet conditions is due to some physicochemical changes which may occur in the presence of water, so that the mechanical behavior does not remain purely elastic.

In order to evaluate the adhesion strength of FF and MMF on biological-like surface, adhesion experiments were performed using wet agar which is commonly used as a representative material for biological tissue. The results confirm that MMF samples still generate higher adhesion strength (between 2 and 3 times greater adhesion) compared to FF samples, even with soft surface material at preload forces of 0.5 and 1 N (see FIG. 11).

Although the invention has been described in conjunction with specific embodiments thereof, it is evident that many alternatives, modifications, and variations will be apparent to those skilled in the art. Accordingly, it is intended to embrace all such alternatives, modifications and variations that fall within the broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A film comprising an array of vertically aligned mushroom-type structures, said film comprising a biodegradable polymer, wherein a ratio between a height dimension and a width dimension of the mushroom-type structures is between 2:1 and 5:1, and wherein said film is characterized by adhesiveness to a biological tissue.

2. The film of claim 1, wherein a density of said vertically aligned structures within said array is between $1.2 \cdot 10^3$ and $1.2 \cdot 10^6 / cm^2$, a center-to-center distance between a pair of adjacent vertically aligned structures within said array is between 1.5 and 150 μm, and/or said width dimension of said vertically aligned mushroom-type structures is between 1 and 100 μm.

3. The film of claim 1, wherein said biodegradable polymer is selected from the group consisting of a polyether, a polyester, a polydioxanone, a polyphosphoester, a polyurethane, and a polyamide or any mixture or a co-polymer thereof.

4. The film of claim 1, wherein said film is characterized by tensile strength of at least 0.5 MPa.

5. The film of claim 1, wherein said adhesiveness is greater by at least 10%, compared to a control.

6. The film of claim 1, wherein at least one surface of said film is characterized by a water contact angle of at least 100°.

7. The film of claim 1, wherein said film comprises a polymeric layer in contact with the vertically aligned mushroom-type structures.

8. The film of claim 1, wherein at least a portion of said film comprises a pharmaceutically active ingredient.

9. The film of claim 8, wherein a w/w concentration of said pharmaceutically active ingredient within said film is between 5 and 50%.

10. The film of claim 8, wherein said pharmaceutically active ingredient is characterized by a log P between 1 and 6.

11. The film of claim 8, wherein said pharmaceutically active ingredient comprises an azole-based compound.

12. The film of claim 8, wherein said film is characterized by a prolonged release time of said pharmaceutically active ingredient.

13. The film of claim 12, wherein said prolonged release time is greater by at least 10%, compared to a control.

14. The film of claim 1, wherein said biological tissue comprises a mucosal tissue.

15. The film of claim 1, wherein said polymer is further in contact with a substrate.

16. A method for administering an active ingredient to a subject, comprising contacting the film of claim 8 with a biological tissue of a subject, thereby administering said active ingredient to said subject.

17. The method of claim 16, wherein said biological tissue comprises a mucosal tissue, a dermal tissue, a muscle tissue, and a urinary bladder tissue or any combination thereof.

18. A method for preventing or treating a medical condition, comprising administering the film of claim 1 to a subject by contacting the film with a biological tissue of said subject, thereby preventing or treating said medical condition.

19. The method of claim 18, wherein said biological tissue comprises a mucosal tissue, a dermal tissue, a muscle tissue, and a urinary bladder tissue or any combination thereof.

20. The method of claim 18, wherein said administering is selected from the group consisting of oral administration including buccal administration and/or sublingual administration, vaginal administration, rectal administration, ocular administration, nasal administration, topical administration and dermal administration, or any combination thereof.

* * * * *